(12) United States Patent
Chen et al.

(10) Patent No.: US 8,221,792 B2
(45) Date of Patent: Jul. 17, 2012

(54) SUSTAINED RELEASE PHARMACEUTICAL COMPOSITIONS FOR HIGHLY WATER SOLUBLE DRUGS

(75) Inventors: Andrew Xian Chen, San Diego, CA (US); David L Bledsoe, Phoenix, AZ (US)

(73) Assignee: Farnam Companies, Inc., Phoenix, AZ (US)

(*) Notice: Subject to any disclaimer, the term of this patent is extended or adjusted under 35 U.S.C. 154(b) by 1247 days.

(21) Appl. No.: 11/482,502

(22) Filed: Jul. 7, 2006

(65) Prior Publication Data

US 2007/0020335 A1  Jan. 25, 2007

Related U.S. Application Data

(60) Provisional application No. 60/697,912, filed on Jul. 7, 2005.

(51) Int. Cl.
*A61K 9/14* (2006.01)
(52) U.S. Cl. .................................................. 424/486
(58) Field of Classification Search .................. 424/486
See application file for complete search history.

(56) References Cited

U.S. PATENT DOCUMENTS

| | | | |
|---|---|---|---|
| 4,218,433 A | 8/1980 | Kooichi et al. | 424/15 |
| 4,839,177 A | 6/1989 | Colombo et al. | 424/482 |
| 5,007,790 A | 4/1991 | Shell | 424/451 |
| 5,120,548 A | 6/1992 | McClelland et al. | 424/473 |
| 5,277,916 A * | 1/1994 | Dwyer et al. | 424/494 |
| 5,366,738 A | 11/1994 | Rork et al. | 424/473 |
| 5,591,452 A | 1/1997 | Miller et al. | 424/468 |
| 5,601,842 A | 2/1997 | Bartholomaeus | 424/464 |
| 5,654,005 A | 8/1997 | Chen et al. | 424/480 |
| 5,919,826 A | 7/1999 | Caruso | 514/629 |
| 6,090,411 A | 7/2000 | Pillay et al. | 424/468 |
| 6,254,887 B1 | 7/2001 | Miller et al. | 424/468 |
| 6,326,027 B1 | 12/2001 | Miller et al. | 424/468 |
| 6,399,096 B1 | 6/2002 | Miller et al. | 424/464 |
| 6,552,031 B1 | 4/2003 | Burch et al. | 514/282 |
| 6,558,701 B2 * | 5/2003 | Bartholomaeus et al. | 424/472 |
| 6,558,704 B1 | 5/2003 | Bartholomaeus et al. | 424/489 |
| 6,576,260 B2 | 6/2003 | Bartholomaeus et al. | 424/469 |
| 7,074,430 B2 | 7/2006 | Miller et al. | 424/468 |
| 2002/0012701 A1 | 1/2002 | Kolter et al. | 424/468 |
| 2003/0044464 A1* | 3/2003 | Ziegler et al. | 424/468 |
| 2003/0104061 A1 | 6/2003 | Bartholomaeus et al. | 424/470 |
| 2003/0143270 A1 | 7/2003 | Deboeck et al. | 424/468 |
| 2003/0180362 A1 | 9/2003 | Park et al. | 424/470 |
| 2003/0219482 A1 | 11/2003 | Chaudhari et al. | 424/469 |
| 2004/0052731 A1 | 3/2004 | Hirsh et al. | 424/10.1 |
| 2004/0096501 A1 | 5/2004 | Vaya et al. | 424/469 |
| 2004/0131671 A1 | 7/2004 | Zhang et al. | 424/458 |
| 2004/0175426 A1 | 9/2004 | Ashton | 424/471 |
| 2004/0259956 A1 | 12/2004 | Wright et al. | 514/650 |
| 2005/0003002 A1 | 1/2005 | Ziegler et al. | 424/468 |
| 2005/0074493 A1 | 4/2005 | Mehta et al. | 424/469 |
| 2005/0182056 A9 | 8/2005 | Pawan et al. | 514/237.5 |
| 2005/0238715 A1 | 10/2005 | Liu et al. | 424/468 |
| 2006/0002860 A1 | 1/2006 | Bartholomaus et al. | 424/10.1 |
| 2006/0099249 A1 | 5/2006 | Seth et al. | 424/464 |
| 2006/0172006 A1 | 8/2006 | Lenaerts et al. | 424/468 |

FOREIGN PATENT DOCUMENTS

| | | |
|---|---|---|
| DE | 199 27 688 A1 | 12/2000 |
| EP | 0 178 138 A2 | 4/1986 |
| EP | 1 166 776 A2 | 1/2002 |
| EP | 1 256 338 A2 | 11/2002 |
| NZ | 516593 | 8/2003 |
| NZ | 516592 | 12/2003 |
| WO | WO 93/04675 A1 | 3/1993 |
| WO | WO 98/17268 A2 | 4/1998 |
| WO | WO 98/47491 A2 | 10/1998 |
| WO | WO 99/01111 A1 | 1/1999 |
| WO | WO 99/03820 A1 | 1/1999 |
| WO | WO 99/13799 A1 | 3/1999 |
| WO | WO 99/61005 A1 | 12/1999 |
| WO | WO 01/13894 A1 | 3/2001 |
| WO | WO 01/15681 A1 | 3/2001 |
| WO | WO 01/15682 A1 | 3/2001 |
| WO | WO 01/15683 A1 | 3/2001 |
| WO | WO 02/066026 A2 | 8/2002 |
| WO | WO 03/072025 A2 | 9/2003 |
| WO | WO 03/072089 A1 | 9/2003 |
| WO | WO 03/080031 A1 | 10/2003 |
| WO | WO 03/105809 * | 12/2003 |
| WO | WO 03/105809 A1 | 12/2003 |
| WO | WO 2004/038428 A2 | 5/2004 |
| WO | WO 2004/064807 A1 | 8/2004 |
| WO | WO 2004/066983 A2 | 8/2004 |
| WO | WO 2004/087175 A1 | 10/2004 |
| WO | WO 2004/110410 A1 | 12/2004 |
| WO | WO 2005/034859 A2 | 4/2005 |
| WO | WO 2006/089707 A1 | 8/2006 |

OTHER PUBLICATIONS

FMC Biopolymer (Avicel Ph-101 specification bulletin).*
Schnitzer (Update of ACR guidelines for osteoarthritis: role of the coxibs. J Pain Symptom Manage. Apr. 2002;23(4 Suppl):S24-30).*
Remington (Remington: The Science and Practice of Pharmacy 19th edition, p. 1612 (1995).*
Ford, J.L., et al., Propranolol hydrochloride and aminophylline release from matrix tablets containing hydroxypropylmethylcellulose, *International Journal of Pharmaceutics* 24:339-350, 1985.
Ford, J.L., et al., Formulation of sustained release promethazine hydrochloride tablets using hydroxypropylmethylcellulose matrices, *International Journal of Pharmaceutics* 24:327-338, 1985.
Ford, J. L., et al., Dissolution of a poorly water soluble drug, indomethacin, from hydroxypropylmethylcellulose controlled release tablets, *Journal of Pharmacy and Pharamacology* 37:33P, 1985.

(Continued)

*Primary Examiner* — Jake M. Vu
(74) *Attorney, Agent, or Firm* — Kilpatrick Townsend & Stockton LLP

(57) ABSTRACT

The present invention provides pharmaceutical compositions for controlled release of pharmaceutically active agents, especially those with a high water solubility, high dose, and/or short half-life. In addition, the present application provides methods for preparing and using such pharmaceutical compositions.

15 Claims, 15 Drawing Sheets

OTHER PUBLICATIONS

Hite, M., et al., Novel Design of a Self-Correcting Monolithic Controlled-Release Delivery System for Tramadol, *Drug Delivery Technology* 3:(2), 2003.

Kukanich, B., et al., Pharmacokinetics of tramadol and the metabolite O-desmethyltramadol in dogs, *J. Vet. Pharmacol. Therap.* 27:239-246, 2004.

Malonne, H., et al., Pharmacokinetic evaluation of a new oral sustained release dosage form of tramadol, *British Journal of Clinical Pharmacology* 57 (3): 270-278, 2003.

Nossol, S., et al., Treatment of pain with sustained-release tramadol 100, 150, 200 mg: results of a post-marketing surveillance study, *Int J Clin Pract* 52 (2):115-121, 1998.

Tiwari, S.B., et al., Controlled Release Formulation of Tramadol Hydrochloride Using Hydrophilic and Hydrophobic Matrix System, *AAPS PharmSciTech* 4 (3):1-6, 2003.

Tramal® SR Sustained Release Tablets, *Consumer Medicine Information*, Grunenthal GmbH, Germany, Jul. 2005.

Velasco, M.V., et al., Influence of drug:hydroxypropylmethylcellulose ratio, drug and polymer particle size and compression force on the release of diclofenac sodium from HPMC tablets, *Journal of Controlled Release*, 57(1):75-85, 1999.

Quoqing, Sun et al., "Studies on Sustained Release Tablets of Tramadol Hydrochloride and its Human Pharmacokinetics," *Journal of China Pharmaceutical University* 27(7):408-411, 1996, (abstract only).

\* cited by examiner

SUSTAINED RELEASE PHARMACEUTICAL COMPOSITIONS FOR HIGHLY WATER SOLUBLE DRUGS

CROSS-REFERENCE TO RELATED APPLICATION

This application claims the benefit under 35 USC 119(e) of U.S. Provisional Patent Application No. 60/697,912, filed Jul. 7, 2005; where this provisional application is incorporated herein by reference in its entirety.

BACKGROUND OF THE INVENTION

1. Field of the Invention

The invention relates to compositions, which provide sustained release (SR), extended release (ER), or controlled release of highly water-soluble pharmaceutically active agents, including those, which are categorized as highly water-soluble, with a short metabolic half-life, and therapeutically efficacious at a high daily dose.

2. Description of the Related Art

It is difficult to provide a sustained release oral dosage form for drugs of a high-solubility, a short half-life, and a high dose. A drug of a high water-solubility can dissolve in water or gastrointestinal milieu readily and tends to release from its dosage form in a burst and thus is absorbed quickly, leading to a sharp increase in the drug blood concentration. Compared to less soluble drugs, it is often difficult to sequester a highly water soluble drug in the dosage form (such as a tablet) and retard the drug release, especially when the drug dose is high.

If the drug of a high water-solubility is also of a short half-life (i.e., quickly metabolized in the body thereby losing its activity), the drug would remain in the blood for only a short time, resulting in a short duration of action. For such a drug, a multiple daily dosing regimen (three, four or more times a day) is necessary to maintain a steady drug concentration in the blood above its effective concentration level. A multiple daily dosing is inconvenient and reduces the patient compliance significantly. A sustained release dosage form, which allows for a reduced dosing frequency such as once a day, is thus much desired.

If the drug of a high water-solubility and a short half-life is also a high dose drug (e.g., those that require a daily dose exceeding 500 mg), it becomes even more challenging to develop sustained release oral dosage forms. For short half-life drugs, to provide a once-a-day tablet, it requires not only that a large amount of drug be incorporated in a dosage unit to provide the daily dose, but also that the dosage units be small in size to allow for ease of swallowing by the human or non-human subject. The requirement for smaller sizes would leave little space in the dosage unit for other ingredients needed to control the release of the drug. The size of the dosage unit becomes even more critical with highly water-soluble drugs since even a larger amount of inactive ingredients (e.g., more than 50% of the total weight) is usually needed to provide the sustained release property, according to the conventional SR methods.

Typically, a tablet of a total weight about 1-1.5 g is considered as the largest tablet that can be readily swallowed by a normal adult patient without discomfort, the same limitation applies to veterinary patients such as dogs. So it is important for an SR composition to have not only high drug content (e.g., more than 50% of the total weight) but also a reasonable size.

In summary, the combined features of a high-solubility, short half-life and high dose poses a great challenge in developing an easy-to-swallow and once-a-day or twice-a-day dosage form for many drugs in the category of high-solubility, short half-life and high dose.

Tablets are by far the most popular dosage form for oral administration. Generally, sustained release tablets have been prepared in a number of ways including matrix tablets, coated tablets and combination thereof. In a matrix tablet, the drug is usually mixed with a gelling material, which upon contact with water can form a thick layer of gel that slows down the diffusion of the drug while undergoing slow erosion. Both diffusion and erosion contribute to drug release. A coating can provide both a barrier limiting the erosion and drug release from its core.

Matrix tablets are probably the most important sustained release form in which the sustain-release components are commonly selected from hydrogel polymers such as cellulose polymer or other synthetic water-soluble polymers such as polyethylene oxides (polyox) or methacrylate polymers (carbomers). Non-ionic cellulose ethers, and more frequently, hydroxypropyl methylcellulose (HPMC, hypromellose) have been widely used for applications in oral SR systems.

Matrix tablets are of particular interest for veterinarian applications because the patients (e.g., dogs, cats, horses, etc.) are likely to chew the tablets. Therefore, a preferable tablet form must be able to withstand some degree of pulverization without losing its sustained-release property. In comparison with a coated sustained release tablet (i.e., sustained release controlled by only or primarily through a layer of coating), matrix tablets are advantageous because an SR coating of a coated sustained release tablet, which is the rpimary barrier, may be destroyed easily by animal chewing, and the bulk of the drug content is thus at risk of being released as a burst, which could be toxic in more serious cases.

SUMMARY OF THE INVENTION

The present invention provides pharmaceutical compositions for controlled release of pharmaceutically active agents and methods for preparing and using such pharmaceutical compositions. The pharmaceutical compositions may have one or more of the following characteristics: (1) providing sustained plasma levels of pharmaceutical active agents, including those of a high water solubility, short half life, and/or high dose; (2) capable of high drug loading (e.g., containing drug content in an amount of about or greater than 50% of the total weight of the pharmaceutical composition); (3) suitable for both human and veterinary uses; and (4) capable of being in a once-a-day or twice-a-day dosage form.

In one aspect, the present invention provides a pharmaceutical composition comprising (i) a pharmaceutically active agent having a high water solubility, a high daily dose, and a short half-life, and (ii) a matrix that comprises a hydrophilic polymer, wherein the pharmaceutically active agent is micronized and dispersed in the matrix.

In certain embodiments, the pharmaceutically active agent contributes about or greater than 15%, 20%, 30%, 40%, 50%, or 60% of the total weight of the pharmaceutical composition.

In certain embodiments, the pharmaceutically active agent has a water solubility of at least about 10 mg/ml, such as at least about 100 mg/ml or about 200 mg/ml.

In certain embodiments, the pharmaceutically active agent is therapeutically effective for a human (e.g., an adult human patient) or non-human subject (e.g., a dog, a cat, a horse, a pig, etc.) at a daily dose of at least about 90 mg, such as at least about 100 mg, 300 mg, or 500 mg.

In certain embodiments, the pharmaceutically active agent is therapeutically effective for a human (e.g., an adult human patient) or non-human subject (e.g., a dog, a cat, a horse, a pig, etc.) at a daily dose of at least about 5 mg/kg of the body weight of the subject, such as at least about 7.5, 10, 12, 14, 16, 18, 20, 25, 30, 35, 40, or 50 mg/kg of the body weight of the subject.

In certain embodiments, the pharmaceutically active agent has a half-life, in an immediate release form, of about or less than 10 hours, such as about or less than 8, 6, or 4 hours in a human (e.g., an adult human patient) or non-human subject (e.g., a dog, cat, house, pig, etc.).

In certain embodiments, the pharmaceutically active agent has a water solubility of about or greater than 100 mg/ml, is therapeutically effective at a daily dose of at least about 90 mg (e.g., at least about 100, 150, 200, 250, 300, 350, 400, 450, or 500 mg), and has a half-life, in an immediate release form, of about or less than 8 hours in a human (e.g., an adult human patient) or non-human subject (e.g., a dog, cat, house, pig, etc.).

In certain embodiments, the pharmaceutically active agent is tramadol, glucosamine, chondroitin, metformin, gabapentin, vitamin C, vitamin B1, vitamin B2, an amino acid, or a pharmaceutically acceptable salt thereof.

In certain embodiments, the pharmaceutically active agent is present the pharmaceutical composition in an amount of about 50% to about 80%, such as about 55% to about 75%, and about 60% to about 70%, by weight.

In certain embodiments, the pharmaceutical composition further comprises a second pharmaceutically active agent. In certain embodiments, the second pharmaceutically active agent is also of a high water solubility, high dose, and/or short half-life.

In certain embodiments, the pharmaceutically active agent is tramadol, glucosamine, or a pharmaceutically acceptable salt thereof, and the second pharmaceutically active agent is chondroitin, a non-steroidal anti-inflammatory drug (NSAID), or a pharmaceutically acceptable salt thereof.

In certain embodiments, the pharmaceutically active agent is tramadol, and the second pharmaceutically active agent is acetaminophen, carprofen, aspirin, or glucosamine.

In certain embodiments, the pharmaceutically active agent is micronized to, or selected from, a size range with an upper size limit of about or less than 210 micron (70 mesh) and a lower limit of about or greater than 63 micron (230 mesh), such as an upper limit of about or less than 177 micron (80 mesh) and a lower limit of about or greater than 74 micron (200 mesh), an upper limit of about or less than 149 micron (100 mesh) and a lower limit of about or greater than 74 micron (200 mesh), and an upper limit of about or less than 125 micron (120 mesh) and a lower limit of about or greater than 74 micron 200 (mesh).

In certain embodiments, the hydrophilic polymer is hydroxypropylmethylcellulose (HPMC), hydroxypropylcellulose, methylcellulose, carboxymethylcellulose, poly(ethylene oxide), alginate, pectin, guar gum, chitosan, carrageenan, starch, dextrin, tragacanth, xanthan gum, povidone, carbomer, or a salt thereof. In certain embodiments, the hydrophilic polymer is present in an amount of about 15% to about 50%, such as about 20% to about 40% and about 20% to about 30%, by weight.

In certain embodiments, the pharmaceutical composition, upon oral administration to a human or non-human patient in need thereof, provides controlled release for at least about 8, 10, 12, 14, 16, 18, 20, 24, 36, 48, 72, 96, 120, 144, or 168 hours.

In certain embodiments, the pharmaceutical composition is suitable for administration to a patient in need thereof no more than twice a day or no more than once a day. In certain embodiments, the pharmaceutical composition is suitable for administration to a patient in need thereof no more than once per day, per two, three, four, five, six, or seven days.

In certain embodiments, the pharmaceutical composition has an in vitro dissolution rate from about 5% to about 40% of the pharmaceutically active agent released after 2 hours, from about 15% to about 55% of the pharmaceutically active agent released after 4 hours, from about 40% to about 80% of the pharmaceutically active agent released after 8 hours, from about 60% to about 95% of the pharmaceutically active agent released after 12 hours, and from about 70% to about 100% of the pharmaceutically active agent released after 18 hours, by weight.

In certain embodiments, the pharmaceutical composition, upon oral administration to a human or non-human patient in need thereof, has an in vitro dissolution rate from about 10% to about 30% of the pharmaceutically active agent released after 2 hours, from about 25% to about 45% of the pharmaceutically active agent released after 4 hours, from about 50% to about 70% of the pharmaceutically active agent released after 8 hours, from about 70% to about 90% of the pharmaceutically active agent released after 12 hours, and from about 80% to about 100% of the pharmaceutically active agent released after 18 hours, by weight.

In certain embodiments, the pharmaceutical composition is in the form of an orally deliverable tablet. In certain embodiments, the tablet comprises a coating (e.g., a release controlling layer or a coating that does not control the release of the drug from the tablet). In certain embodiments, the coating layer constitutes about 1% to about 5% (e.g., about 1% to about 2%) by weight of the tablet. In certain embodiments, the tablet further comprises a tableting binder, a filler, and/or a lubricating agent.

In certain embodiments, the tablet maintains its in vitro sustained release property even after broken into two or more pieces. In certain embodiments, the tablet maintains its in vivo sustained release property even after being breaking into two or more pieces.

In certain embodiments, the pharmaceutical composition is in the form of a fragmented or crushed matrix tablet. In certain embodiments, the composition in the form of a fragmented or crushed matrix tablet, upon oral administration, provides controlled release for at least about 8, 10, 12, 14, 16, 18, 20, 24, 36, 48, 72, 96, 120, 144, or 168 hours.

In certain embodiments, the composition, upon oral administration to a patient in need thereof, provides a plasma concentration at or above a therapeutically effective concentration for a period of time that is at least about 100%, 150%, 200%, or 250% longer than an immediate release formulation containing the same amount of the pharmaceutically active agent.

In certain embodiments, the composition, upon oral administration to a patient in need thereof, provides an Area Under the Curve (AUC) (0 to infinity) (plasma concentration versus time) at least about 50%, 100%, 150%, 200%, or 250% higher than the AUC (0 to infinity) provided by an immediate release formulation containing the same amount of the pharmaceutically active agent.

In certain embodiments, the pharmaceutically active agent is tramadol, and upon oral administration in a dog, the pharmaceutical composition provides an AUC (0 to infinity) (plasma concentration versus time) of tramadol about or greater than 2, 4, or 6 µg hr/mL. In certain embodiments, such a pharmaceutical composition, upon oral administration in a dog, further provides a $C_{max}$ (maximum concentration) of tramadol of about or less than 10 µg/mL.

In certain embodiments, the pharmaceutically active agent is tramadol, and upon oral administration in a dog, the pharmaceutical composition provides an AUC (0 to infinity) (plasma concentration versus time) of the active metabolite of tramadol, M1 (O-desmethyltramadol), about or greater than 0.2, 0.4, 0.6, 0.8, 1.0, or 1.2 μg hr/mL. In certain embodiments, such a pharmaceutical composition, upon oral administration in a dog, further provides a $C_{max}$ of M1 of about or less than 2 μg/mL.

In another aspect, the present invention provides a pharmaceutical composition in the form of an orally deliverable tablet comprising tramadol hydrochloride having an upper size limit of about or less than 125 micron (120 mesh) and a lower size limit of about or greater than 74 micron (200 mesh) in an amount of about 75 mg to about 1000 mg (e.g., about 90, 100, 180, 200, 300, 400, 500, 600, 700, 800, 900, or 1000 mg), dispersed in a matrix comprising (a) HPMC of a high molecular weight in an amount of about 20% to about 30% by weight of the tablet, (b) a microcrystalline cellulose having a particle size of about or less than 210 micron, in an amount of about 10% to about 20% by weight of the tablet, and (c) a tableting lubricant in an amount of about 1% to about 3% by weight of the tablet.

In another aspect, the present invention provides a pharmaceutical composition in the form of an orally deliverable tablet comprising tramadol hydrochloride having an upper size limit of about or less than 125 micron (120 mesh) and a lower size limit of about or greater than 74 micron (200 mesh) in an amount of about 150 mg to about 500 mg (e.g., about 150, 200, 250, 300, 350, 400, 450, or 500 mg), dispersed in a matrix comprising (a) HPMC of a high molecular weight in an amount of about 20% to about 40% by weight of the tablet, (b) a microcrystalline cellulose having a particle size of about or less than 210 micron, in an amount of about 10% to about 30% by weight of the tablet, and (c) a tableting lubricant in an amount of about 1% to about 3% by weight of the tablet.

In another aspect, the present invention provides a pharmaceutical composition in the form of an orally deliverable tablet comprising glucosamine hydrochloride having an upper size limit of about or less than 125 micron (120 mesh) and a lower size limit of about or greater than 74 micron (200 mesh) in an amount of about 500 mg to about 1000 mg (e.g., about 500, 600, 700, 800, 900, or 1000 mg), and chondroitin sulfate having an upper size limit of about or less than 210 micron (70 mesh), in an amount of about 300 mg to about 1000 mg, dispersed in a matrix comprising (a) HPMC of a high molecular weight in an amount of about 20% to about 30% by weight of the tablet, (b) a binder having a particle size of about or less than 210 micron, in an amount of about 2% to about 20% by weight of the tablet, and (c) a tableting lubricant in an amount of about 1% to about 3% by weight of the tablet.

In another aspect, the present invention provides a pharmaceutical composition in the form of an orally deliverable tablet comprising glucosamine hydrochloride having an upper size limit of about or less than 125 micron (120 mesh) and a lower size limit of about or greater than 74 micron (200 mesh) in an amount of about 500 mg to about 1500 mg (e.g., about 500, 600, 700, 800, 900, 1000, 1100, 1200, 1300, 1400, or 1500 mg), dispersed in a matrix comprising (a) HPMC of a high molecular weight in an amount of about 20% to about 30% by weight of the tablet, (b) a binder having a particle size of about or less than 210 micron, in an amount of about 2% to about 20% by weight of the tablet, and (c) a tableting lubricant in an amount of about 1% to about 3% by weight of the tablet.

In another aspect, the present invention provides a pharmaceutical composition in the form of an orally deliverable tablet comprising gabapentin having an upper size limit of about or less than 125 micron (120 mesh) and a lower size limit of about or greater than 74 micron (200 mesh) in an amount of about 300 to about 1500 mg (e.g., about 300, 400, 500, 600, 700, 800, 900, 1000, 1100, 1200, 1300, 1400, or 1500 mg), dispersed in a matrix comprising (a) HPMC of a high molecular weight in an amount of about 20% to about 30% by weight of the tablet, (b) a binder having a particle size of about or less than 210 micron, in an amount of about 2% to about 20% by weight of the tablet, and (c) a tableting lubricant in an amount of about 1% to about 3% by weight of the tablet.

In another embodiment, the present invention provides a pharmaceutical composition in the form of an orally deliverable tablet comprising acetaminophen having an upper size limit of about or less than 125 micron (120 mesh) and a lower size limit of about or greater than 74 micron (200 mesh) in an amount of about 300 mg to about 1500 mg (e.g., about 300, 400, 500, 600, 700, 800, 900, 1000, 1100, 1200, 1300, 1400, or 1500 mg), dispersed in a matrix comprising (a) HPMC of a high molecular weight in an amount of about 20% to about 30% by weight of the tablet, (b) a binder having a particle size of about or less than 210 micron, in an amount of about 2% to about 20% by weight of the tablet, and (c) a tableting lubricant in an amount of about 1% to about 3% by weight of the tablet.

In another aspect, the present invention provides a pharmaceutical composition in the form of an orally deliverable tablet comprising metformin hydrochloride having an upper size limit of about or less than 125 micron (120 mesh) and a lower size limit of about or greater than 74 micron (200 mesh) in an amount of about 300 to about 1500 mg (e.g., about 300, 400, 500, 600, 700, 800, 900, 1000, 1100, 1200, 1300, 1400, or 1500 mg), dispersed in a matrix comprising (a) HPMC of a high molecular weight in an amount of about 20% to about 30% by weight of the tablet, (b) a binder having a particle size of about or less than 210 micron, in an amount of about 2% to about 20% by weight of the tablet, and (c) a tableting lubricant in an amount of about 1% to about 3% by weight of the tablet.

In certain embodiments, the above-described tablet is optionally coated with a layer of film using a coating composition comprising an aqueous dispersion containing ethyl cellulose, oleic acid, ammonium hydroxide and water and a solution containing polyethylene glycol.

In certain embodiments, the tablets described herein are processed by a direct compression method.

In certain embodiments, the pharmaceutical compositions (e.g., intact, fragmented, or crushed matrix tablets) described herein are adapted for delivery to humans (e.g., adult human patients) or veterinary subjects (e.g., dogs, cats, horse, pigs, etc.).

In another aspect, the present invention provides a process for preparing a sustained-release pharmaceutical composition in a form of an orally deliverable tablet wherein the process comprising (a) micronizing a pharmaceutically active agent, (b) selecting the pharmaceutically active agent having an upper size limit of about or less than 125 micron (120 mesh) and a lower size limit of about or greater than 74 micron (200 mesh), (c) dry blending the pharmaceutically active agent from step (b) with a hydrophilic polymer and a binder, (d) admixing the mixture of step (c) with a lubricant, a glidant, or both, (e) compressing the mixture of step (d) into tablets (e.g., those of hardness of about 10 to about 20 kp), and (f) optionally coating the tablets (e.g., using a spray pan coater or a fluid bed processor).

These and other embodiments of the invention will become apparent from the detailed description below.

BRIEF DESCRIPTION OF THE DRAWINGS

FIG. 3A: uncoated 600 mg tablets (administered as ½ tablets broken along a score). FIG. 3B: coated 600 mg tablets (administered as ½ tablets broken along a score)

DETAILED DESCRIPTION OF THE INVENTION

Figure 1:
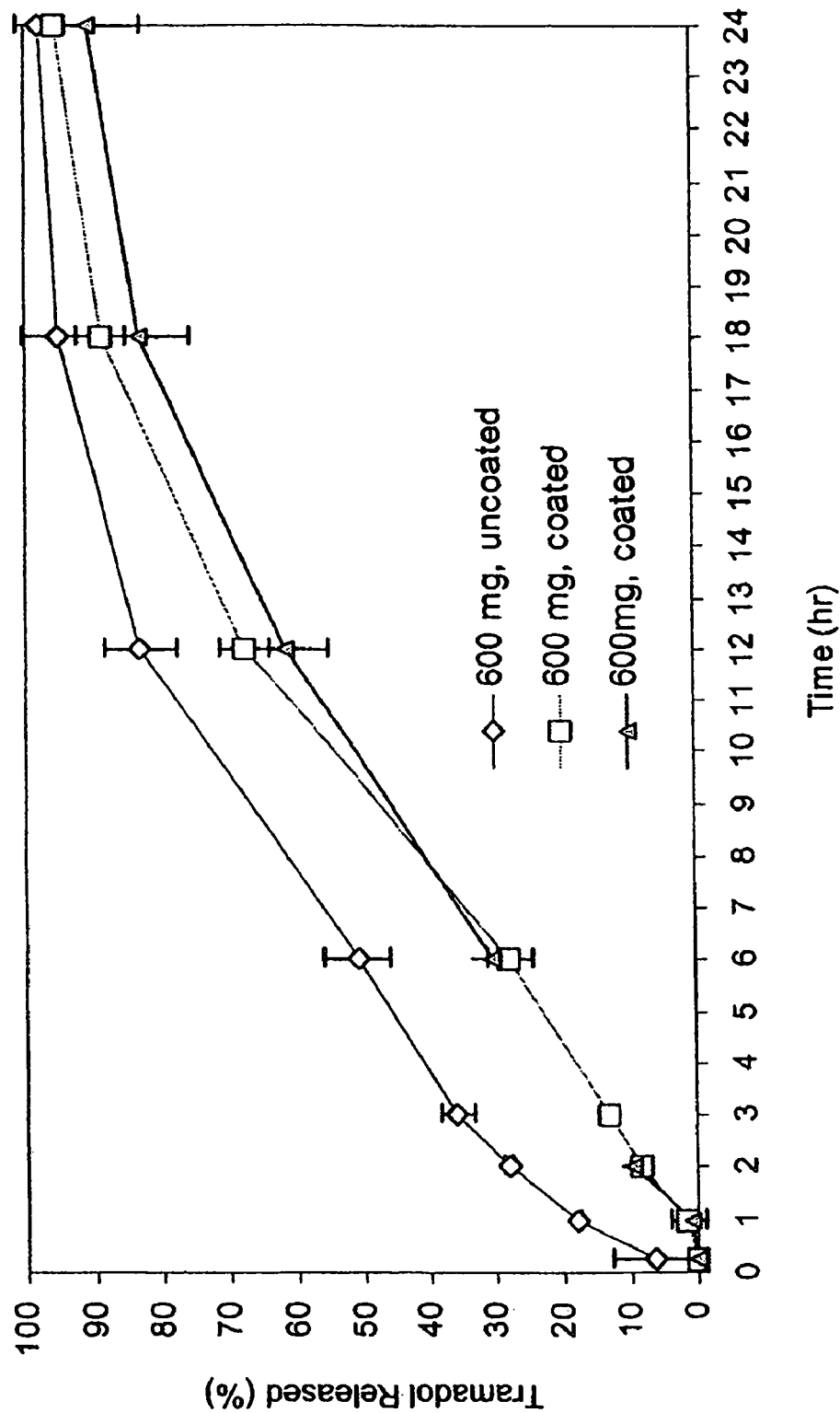
FIG. 1 is a graph depicting the in vitro release of tramadol hydrochloride from (a) an uncoated matrix SR tablet (1 lot), with (b) a coated matrix SR tablet (2 lots) prepared according to Example 1 of the present application using a micronized tramadol HCl drug substance. The SR tablets released their entire drug content in about 12-16 hours from the uncoated tablets and in about 18-24 hours from the coated tablets.

The present invention provides pharmaceutical compositions for controlled release of pharmaceutically active agents, especially those with a high water solubility, high dose, and/or short half-life. In addition, the present application provides methods for preparing and using such pharmaceutical compositions.

In one aspect, the present invention provides a pharmaceutical composition comprising (i) a pharmaceutically active agent having a high water solubility, a high daily dose, and a short half-life, and (ii) a matrix that comprises a hydrophilic polymer, wherein the pharmaceutically active agent is micronized and dispersed in the matrix.

In certain embodiments, the pharmaceutical composition of the present invention is in the form of an orally deliverable tablet (i.e., an orally deliverable matrix tablet). In certain other embodiments, the pharmaceutical composition of the present invention is in the form of a fragmented or crushed matrix tablet.

"Matrix tablets" refers to tablet dosage forms in which a drug is substantially homogenously dispersed in a polymer in association with conventional excipients. This admixture is typically compressed under pressure to produce a tablet. The drug is released from the tablet by diffusion and erosion. Matrix tablet systems are described in detail in The Handbook of Pharmaceutical Controlled Release Technology, D. L. Wise (ed.), Marcel Dekker, Inc., New York (2000) and Treatise on Controlled Drug Delivery: Fundamentals, Optimization, and Applications, A. Kydonieus (ed.), Marcel Dekker, Inc., New York, (1992).

The term "matrix" refers to the combination of the components of a matrix tablet other than the drug or the coating. It comprises primarily one or more polymers and may comprise other excipients.

The term "pharmaceutically active agents" (used interchangeably with "drugs") refers to compounds or compositions, including plant extracts, herbal powders, minerals, or naturally occurring ingredients, that have beneficial pharmaceutical, nutritional, therapeutic, or cosmetic effects.

A pharmaceutically active agent of a "high water solubility," or that is "highly soluble" or "highly water soluble," refers to a pharmaceutically active agent (in its free base, free acid or salt form) having solubility in water in excess of about 10 mg/ml at room temperature (20-25°). In certain embodiments, the pharmaceutically active agent of the present invention has a water solubility of about or greater than 20, 30, 40, 50, 60, 70, 80, 90, 100, 120, 140, 160, 180, 200, or 250 mg/mL at room temperature.

A pharmaceutically active agent of a high daily dose refers to a pharmaceutically active agent that is orally administered at a dose of about or greater than 75 mg to a human (e.g., an adult human patient) or non-human subject (e.g., a dog, cat, house, pig, etc.). In certain embodiments, the pharmaceutically active agent of the present invention has a daily dose about or greater than 90, 100, 200, 250, 300, 350, 400, 450, or 500 mg for a human (e.g., an adult human patient) or non-human subject (e.g., a dog, cat, house, pig, etc.). Exemplary pharmaceutically active agents of a high dose include tramadol (100 mg/dose or more), acyclovir (200 mg/dose), acetaminophen (300 mg/dose), metformin (500 mg/dose), gabapentin (100-800 mg/dose), glucosamine (500 mg/dose), etc.

In certain embodiments, the pharmaceutically active agent is therapeutically effective for a human (e.g., an adult human patient) or non-human subject (e.g., a dog, a cat, a horse, a pig, etc.) at a daily dose of at least about 5 mg/kg of the body weight of the subject, such as at least about 7.5, 10, 12, 14, 16, 18, 20, 25, 30, 35, 40, or 50 mg/kg of the body weight of the subject.

The term "half-life" of a pharmaceutically active agent refers to the time in which the plasma concentration of the pharmaceutically active agent in a human (e.g., an adult human patient) or non-human subject (e.g., a dog, cat, horse, pig, etc.) to which the pharmaceutically active agent is administered is reduced by half when the pharmaceutically active agent is administered in an immediate release form.

A pharmaceutically active agent of a "short half-life" refers to a pharmaceutically active agent that has a half-life about or less than 10 hours. In certain embodiments, the pharmaceutically active agent of the present invention has a half-life of about or less than about 9, 8, 7, 6, 5, 4, 3, or 2 hours in a human (e.g., an adult human patient) or non-human subject (e.g., a dog, cat, horse, pig, etc.). In general, a pharmaceutically active agent of a short half-life is required to be taken more than twice a day in its immediate release forms to maintain the efficacious blood concentration level through the day.

A pharmaceutically active agent of a high water solubility, a high daily dose and a short half-life refers to a drug that meets all three requirements for being of (1) a high water solubility, (2) high daily dose, and (3) short half-life. In certain embodiments, the pharmaceutically active agent of the present invention has a water solubility of about or greater than 100 mg/ml, is therapeutically effective at a daily dose of about or greater than 90 mg (e.g., about or greater than 100, 150, 200, 250, 300, 350, 400, 450, or 500 mg), and has a half-life, in an immediate release form, of about or less than 8 hours in a human (e.g., an adult human patient) or non-human subject (e.g., a dog, cat, horse, pig, etc.).

Examples of drugs of high water solubility, short half-life, and high dose include, but not limited to: verapamil HCl, potassium chloride, cefdnir, propafenone HCl, hydroxyurea, hydrocodone bitartrate, delavirdine mesylate, nelfinavir meslyate, pentosan polysulfate sodium, tocainide HCl, quetiapine fumarate, fexofenadine HCl, carafate, rifampin, moxifloxacin HCl, praziquantel, ciprofloxacin, phosphate sodium potassium, methenamine mandelate, sotalol HCl, cefprozil, cefadroxil, metformin HCl, irbesartan, nefazodone HCl, gatifloxacin, didanosine, modafinil, efavirenz, metaxalone, amantadine HCl, morphine sulfate, mefenamic acid, diltiazem HCl, sevelamer HCl, albendazole, amoxicilline, clavulanate potassium, lithium carbonate, lamivudine, sumatriptan succinate, nabumetone, zidovudine, cimetidine, chlorpromazine HCl, valacyclovir HCl, bupropion HCl, ranitidine, abacavir sulfate, acyclovir, aminobenzoate potassium, pyridostigmine bromide, potassium chloride, isosorbide mononitrate, nicin, demeclocycline HCl, cefixime, naproxen sodium, tetratcycline HCl, cefuroxime axetil, propoxyphene napsylate, pyrazinamide, flecainide acetate, simethicone, mebendazole, methdopa, chlorathiazide, indinavir, penicillamine, meyyrosine, losartan potassium, thiobendazole, norfloxacin, hydroxyurea, procainamide, entacapone, valsartan, terbinafine HCl, metaprolol tartrate, ofloxacin, levofloxacin, chlorzoxazone, tolmetin sodium, tramadol HCl, bepridil HCl, phenytoin sodium, atorvastatin calcium, gabapentine, celecoxib, fluconazole, doxepine HCl, trovafloxacin mesylate, azithromycin, sertraline HCl, rifabutin, cefpodoxime proxetil, mesalamine, etidronate disodium, nitrofurantoin, choline magnesium trisalicylate, theophylline, nizatidine, pancreatin, quinidine sulfate, methocarbamol, mycophenolate mefetil, ganciclovir, saquinavir mesylate, tolcapne, ticlopidine HCl, valganciclovir HCl, capecitabine, orlistat, colsevelam HCl, irbesartan, succimer, meperidine HCl, hydroxychloroquine sulfate, guaifenesine, eprosartan mesylate, aminodarone HCl, felbamate, pseudoephedrine sulfate, carisoprodol, venlafaxine, propanolol HCl, etodolac, acebutolol, chondrotin, pyruvate, water soluble vitamins, creatine, Isoflavone, betaine HCl, psyllium, pantothenic Acid, zinc chloride, zinc gluconate, zinc sulfate, hytoestrogen, pycnogenol, proanthocyanidin, suntheanine, methylsulfonyl-methane, L-glutamine, colostrums, biotin, acetyl-L-carnitine, inositol, L-tyrosine, s-adenosyl methionine, bromelain, 2-dimethylaminoethanol, chromium picolinate, and combinations thereof.

Additional examples of drugs of a high water solubility, short half-life, and high dose include, but not limited to, amino acids, sugars, carbohydrates, proteins, saccharides, phospholipids, ginkgo biloba, standardized St. John's Wort, standardized Echinacea, yeasts, enzymes, bacteria, and combinations thereof.

In certain embodiments, the pharmaceutically active agents useful in the present invention is tramadol HCl, acyclovir, glucosamine, chondroitin, acetaminophen, metformin, gabapentin, vitamin C, vitamin B's, amino acids, or a pharmaceutically acceptable salt thereof.

A "pharmaceutically acceptable salt" of a pharmaceutically active agent refers to a salt of the pharmaceutically active agent, within the scope of sound medical judgment, suitable for use in contact with the tissues of humans and lower animals without undue toxicity, irritation, allergic response, and the like, and effective for the intended use of the pharmaceutically active agent.

In certain embodiments, the pharmaceutical compositions of the present invention further comprise one or more other pharmaceutically active agents. In certain embodiments, the other pharmaceutically active agents may also be of a high water solubility, high dose, and/or short half-life. For example, in certain embodiments, the pharmaceutical compositions of the present invention comprise glucosamine hydrochloride and chondroitin sulfate, tramadol hydrochloride and glucosamine hydrochloride, or tramadol hydrochloride and acetaminophen. In certain other embodiments, the other pharmaceutically active agents may not be of high water solubility, high dose and/or short half-life.

In certain embodiments, the other pharmaceutically active agent may have a same or similar pharmaceutical effect as the pharmaceutically active agent of a high water solubility, high dose, and/or short half-life in a pharmaceutical composition. For instance, a pharmaceutical composition of the present invention may comprise tramadol and another analgesic agent. In certain embodiments, the other pharmaceutically active agent may have a pharmaceutical effect different from the pharmaceutically active agent of a high water solubility, high dose, and/or short half-life in a pharmaceutical composition. For instance, a pharmaceutical composition of the present invention may comprise tramadol and an antibacterial compound.

In the embodiments where a pharmaceutical composition comprises two or more drugs that produce an additive pharmaceutical effect, the amount of each drug is generally lower than that used for each drug in monotherapy (i.e., when the drugs are given alone). For example, in one embodiment, the dose of each drug in the composition may be from 0.1 to 0.75 of the dose used in monotherapy, such as from 0.25 to 0.75 of the dose used in monotherapy. In another embodiment, the dose of one drug is one quarter of its normal dose used in monotherapy, and the dose of the other drug is three quarters of its normal dose used in monotherapy. In another embodiment, the dose of each drug is approximately one half of its normal dose when used in monotherapy.

In the embodiments where a pharmaceutical composition comprises two or more drugs that produce a synergistic pharmaceutical effect, the combined dose of the drugs is lower than that if the two drugs produce only an additive pharmaceutical effect. For example, in one embodiment, the dose of one drug is one quarter of its normal dose used in monotherapy, and the dose of the other drug is also quarter of its normal dose used in monotherapy.

In the embodiments where a pharmaceutical composition comprises two or more drugs that produce different pharmaceutical effects, the amount of each drug should be sufficient to produce the intended effect of the drug. In most of embodiments, the dose of each drug is similar to that used in monotherapy. In certain other embodiments, the dose of each drug may be higher or lower than that used in monotherapy.

The weight ratio of a drug of a high water solubility, short half-life, and/or high dose to another drug in a pharmaceutical composition of the present invention depend on both drugs and their dosages used in monotherapy. In certain embodiments, the weight ratio of a drug of high water solubility, short half-life, and/or high dose to another drug in a pharmaceutical composition is from about 1:1000 to 1000:1, such as 1:100 to 100:1, 1:50 to 50:1, 1:10 to 10:1, 1:5 to 5:1, 1:2 to 2:1, 1:1 to 1:10, 1:1 to 1:50, 1:1 to 1:100, 100:1 to 1:1, 50:1 to 1:1, or 10:1 to 1:1.

In certain embodiments, the pharmaceutical composition comprises tramadol and another analgesic agent. For example, in certain embodiments, the pharmaceutical composition comprises tramadol and an opioid analgesic. In certain other embodiments, the pharmaceutical composition comprises tramadol and a non-steroidal anti-inflammatory drug (NSAID).

Exemplary opioid analgesics that may be included in tramadol-containing pharmaceutical compositions include, but are not limited to, alfentanil, alphaprodine, anileridine, apomorphine, betaprodine, buprenorphine, butorphanol, carfentanil, codeine, codeinone, cyclorphan, cylcazocine, dextromethorphan, dextropropoxyphene, diamorphine (heroin), dihydrocodeine, diphenoxylate, ethoheptazine, etorphine, fentanyl, hydrocodone, hydromorphone, isomethadone, levallorphan, levorphanol, loperamide, meperidine, methadone, metopon, morphine, morphinone, nalbuphine, normorphine, N-(2-phenylethyl)-normorphine, oxycodone, oxymorphone, pentazocine, pethidine (meperidine), phenazocine, piminodine, propoxyphene, racemorphan, remifentanil, and sufentanil.

Exemplary NSAIDs that may be included in tramadol-containing pharmaceutical compositions include, but are not limited to, aspirin, carprofen, deracoxib, etodolac, firocoxib, celecoxib, diclofenac, diflunisal, fluriprofen, ibuprofen, indomethacin, ketoprofen, kietorolac, mefenamic acid, meloxicam, naproxen, piroxicam, rofecoxib, sulindac, and valdecoxib.

In certain embodiments, the pharmaceutical compositions of the present invention comprise both tramadol and acetaminophen. In a certain embodiment, the weight ratio of tramadol to acetaminophen in the composition is from about 1:10 to about 1:5.

In certain embodiments, the pharmaceutical compositions of the present invention comprise both tramadol and diclofenac. In a certain embodiment, the weight ratio of tramadol to diclofenac is about 1:4 to 4:1, such as 1:2 to 3:1, and 1:1 to 2.5:1.

In certain embodiments, the pharmaceutical compositions of the present invention comprise both tramadol and aspirin. In a certain embodiment, the weight ratio of tramadol to aspirin is about 1:4 and 4:1, such as between 1:2 and 2:1. In certain embodiments, the pharmaceutical compositions of the present invention comprise both tramadol and carprofen. In a certain embodiment, the weight ratio of tramadol to carprofen is about 3:1 to 10:1.

In certain embodiments, the pharmaceutical compositions of the present invention comprise both tramadol and flupirtine. In a certain embodiment, the weight ratio of tramadol to flupirtine is about 1:1 to 1:5.

In certain embodiments, the pharmaceutical compositions of the present invention comprise both tramadol and codeine or oxycodone. In a certain embodiment, the weight ratio of tramadol to codeine or oxycodone is about 1:20 to about 20:1, such as sbout 1:2 to about 2:1 and about 1:1 to 2:1.

In certain embodiments, the pharmaceutical compositions of the present invention comprise both tramadol and a NSAID, wherein the weight ratio of tramadol to the NSAID is about 1:1 to about 1:200, from about 1:2 to about 1:200, and about 1:2 to about 1:20.

In certain embodiments, the pharmaceutical compositions of the present invention comprise both tramadol and a calcium channel antagonist (e.g., nimodipine, nicardipine, nifedipine, diltiazem, verapamil, gallopamil, flunarizine, and cinnarizine). In a certain embodiment, the weight ration of tramadol to the calcium channel antagonist is about 200:1 to about 5:1.

In certain embodiments, the tramadol-containing pharmaceutical compositions of the present invention further comprise ketoprofen, cyproheptadine (serotonin antagonist), prozosin ($\alpha$-adrenoceptor antagonist), clonidine ($\alpha$-2-adrenoceptor agonist), clomipramine (selective inhibitor of serotonin neuronal uptake), or xylamine (selective irreversible inhibitor of norepinepherine uptake).

In certain embodiments, the pharmaceutical compositions of the present invention comprise glucosamine and an analgesic, such as a NSAID. Exemplary NSAIDs include, but are not limited to, aspirin; phenylbutazone, oxyphenbutazone, antipyrine, aminopyrine, dipyrone and apazone; indomethacin; sulindac; fenamates such as mefenamic, meclofenamic, flufenamic, tolfenamic and etofenamice acids; aryl acetic acid and propionic acid compounds such as 2-(p-isobutylphenyl)propionic acid (ibuprofen); alphamethyl-4-(2-thienylcarbonyl)benzene acetic acid (suprofen); 4,5-diphenyl-2-oxazole propionic acid (oxprozin); rac-6-chloro-alphamethyl-carbazole-2-acetic acid (carprofen); 2-(3-phenyloxyphenyl)-propionic acid, particularly the calcium salt dihydrate thereof (fenoprofen and fenoprofen calcium); 2-(6-methoxy-2-naphthyl)propionic acid (naproxen); 4-(1,3-dihydro-1-oxo-2H-isoindol-2-yl)-$\alpha$-methylbenzene acetic acid (indoprofen); 2-(3-benzoylphenyl)propionic acid (ketoprofen); and 2-(2-fluoro-4-biphenylyl)propionic acid (flurbiprofen) and 1-5-(4-methylbenzoyl)-1H-pyrrole-2-acetic acid (tolmetin). Additional exemplary NSAIDs are compounds within the class including sodium 5-(4-chlorobenzoyl)-1,4-dimethyl-1H-pyrrole-2-acetate dihydrate (zomepirac sodium); 4-hydroxy-2-methyl-N-(2-pyridyl-2H-1,2-benzothiazine-3-carboxamide-1,1-dioxide (piroxicam); 2',4'-difluoro-4-hydroxy-3-biphen-ylcarboxylic acid (diflunisal) or 1-isopropyl-7-methyl-4-phenyl-2(1H)-quinozolinone (proquazone), and Cox-2 inhibitors such as rofecoxib and celecoxib.

In certain embodiments, the weight ratio of glucosamine to the analgesic in the above pharmaceutical compositions is from about 1:10 to about 100:1, such as from about 1:1 to about 20:1, and about 1:2 to about 10:1.

In certain embodiments, the glucosamine-containing pharmaceutical compositions of the present invention further comprise ibuprofen, diclofenac, tramadol, or acetaminophen. In certain embodiments, the weight ratio of glucosamine to ibuprofen, diclofenac, tramadol, or acetaminophen is from about 1:10 to about 100:1, such as from about 1:1 to about 20:1, and about 1:2 to about 10:1.

In certain embodiments, the pharmaceutical composition of the present invention comprises glucosamine (e.g., glucosamine hydrochloride and glucosamine sulfate), hydrolyzed collagen, and a bioflavanol (e.g., proanthocyanidin, leucocyanidin, pcynogenol, and those extracted from grape seeds, pine bark or turmeric root).

It is generally difficult to provide a sustained release oral dosage form for drugs of a high-solubility, short half-life, and high dose. Highly water-soluble drug substances are difficult to sequester in a solid dosage form and often released quickly in a burst in the gastrointestinal tract, leading to sharp increases and subsequent decreases in plasma level concentrations. A relatively large amount of release controlling ingredients is needed to slow down or sustain the release of a highly water-soluble drug.

When such a highly water-soluble drug substance is also metabolized quickly in vivo, it would require multiple dosing to maintain the drug in blood at a concentration above its effective concentration level. To prepare a once-a-day dosage form, a total amount of drug required for the daily dose, along with the required inactive ingredients needed for fabricating the once-a-day dosage form, would become too much for a patient to swallow.

For example, tramadol, having the structure set forth below and the systematic (IUPAC) name of rac-(1R,2R)-2-(dimethylaminomethyl)-1-(3-methoxyphenyl)-cyclohexanol, is a centrally acting analgesic and has a short half-life (5.6-7.0 hours in human and 0.8-1.7 hours in dogs). It is available as a hydrochloric acid salt, which is highly water soluble. The current human tablet formulation (ULTRAM® by Ortho-McNeil) is dosed at a high frequency, i.e., 50-100 mg every six hours or 4 times a day. It is estimated that a once-a-day tablet would require 400-500 mg of tramadol be formulated in a tablet with a total weight less than 1000 mg, such as less than 800 mg for ease of swallowing.

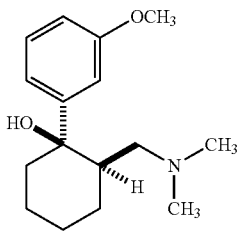

In a veterinary application, it was reported by KuKanich & Papich (J. Vet. Pharmacol. Therap. 27, 239-46, 2004) that 5 mg/kg dose at every 6 hours (i.e., 4 times a day) was predicated to achieve a plasma concentrations of tramadol and its active metabolite M1 consistent with analgesia in humans. It is estimated that a dose of 15 mg/kg or more would be needed for once-a-day sustained-release tablets, which translates to a dose of 150, 300, and 450 mg for a dog of body weight of 10, 20 and 30 kg, respectively.

Furthermore, when such a highly water-soluble and fast metabolizing drug substance also happens to be a high dose drug, i.e., requires a high dose to be therapeutically effective, it would make a once-a-day dosage form even more difficult using conventional formulation techniques. With the current art known to those in the field of pharmaceutical sciences, to achieve such dosing, one almost always ends up with a very large tablet or capsule (i.e., too big to swallow) or a large quantity of tablets or capsules (i.e., too many to swallow). The reason is that the current sustained release techniques require a relatively large amount of inactive ingredients, e.g., more than 50% of the total dosage weight, to provide the appropriate sustained release for the active drug. The large amount of inactive ingredients inevitably increases the total size (weight) of the tablet or capsule to a level that is too big to swallow.

This invention, in certain embodiments, discloses a new composition and method of preparing the composition (e.g., a matrix tablet) in which the inactive ingredients are reduced to less than about 50%, such as to less than about 45%, 40%, 35%, or 30% of the total weight of the composition. By reducing the amount of inactive ingredients used, the pharmaceutical composition (e.g., the matrix tablet) of this invention is capable of delivering, in a once-a-day or twice-a-day dosage form (e.g., a once-a-day or twice-a-day tablet), a drug of a high water solubility, short half-life and high dose, wherein the amount of the drug in each dosage form can be more than about 500 mg, such as more than about 600, 700, 800, 900, 1000, 1100, or 1200 mg, while the total tablet weight is kept at about 1000 to 1500 mg or less and the size of the dosage form appropriate for swallowing by a normal human or non-human subject.

One approach used in the present invention to minimizing the amount of inactive ingredients while maintaining sustained release of drugs in a pharmaceutical composition is to select drug particles from a specific particle size range as described in detailed below.

Particle size of the drug substance (raw material) is customarily defined by an upper limit of particle size (e.g., 90-95% of drug particles is less than 210 micrometer). It is also common to see that a bulk of drug substance powder is specified by its ability to pass a sieve of certain size (mesh) (e.g., 90-95% of drug particles pass a 70-mesh sieve). Common drug particle sizes and useful sieve types are listed in the table below:

| Sieve Designation | Nominal Sieve Opening | | |
|---|---|---|---|
| Mesh | Inches | mm | Microns |
| No. 40 | 0.0165 | 0.420 | 420 |
| No. 45 | 0.0139 | 0.354 | 354 |
| No. 50 | 0.0117 | 0.297 | 297 |
| No. 60 | 0.0098 | 0.250 | 250 |
| No. 70 | 0.0083 | 0.210 | 210 |
| No. 80 | 0.0070 | 0.177 | 177 |
| No. 100 | 0.0059 | 0.149 | 149 |
| No. 120 | 0.0049 | 0.125 | 125 |
| No. 140 | 0.0041 | 0.105 | 105 |
| No. 170 | 0.0035 | 0.088 | 88 |
| No. 200 | 0.0029 | 0.074 | 74 |
| No. 230 | 0.0025 | 0.063 | 63 |
| No. 270 | 0.0021 | 0.053 | 53 |
| No. 325 | 0.0017 | 0.044 | 44 |
| No. 400 | 0.0015 | 0.037 | 37 |

The particle size of the drug substance to be used in the pharmaceutical composition (e.g., the matrix tablet) of this invention is considerably smaller than conventional particle size and is in a range having an upper size limit of about or less than 210 micron (70 mesh) and a lower limit of about or greater than 63 micron (230 mesh), such as an upper limit of about or less than 177 micron (80 mesh) and a lower limit of about or greater than 74 micron (200 mesh), an upper limit of about or less than 149 micron (100 mesh) and a lower limit of about or greater than 74 micron (200 mesh), and an upper limit of about or less than 125 micron (120 mesh) and a lower limit of about or greater than 74 micron (200 mesh).

An "upper size limit" or an "upper limit" of a drug substance refers to a size that greater than 95% by weight drug substance particles are under.

A "lower size limit" or a "lower limit" of a drug substance refers to a size that greater than 95% by weight drug substance particles are above.

Drug substance particles in the above-noted size ranges (e.g., a range having an upper size limit of about or less than 210 micron (70 mesh) and a lower limit of about or greater than 63 micron (230 mesh)) are regarded as "fine particles" or "micronized particles", as most commercially available drug substances are provided in a particle size range above the most typical size ranges for this invention. The inventors of this application have found that drug particles with size greater than the aforementioned preferable upper size limit would fail to produce the desired sustained release property, while drug particles with size smaller than the aforementioned preferable lower size limit would have poor compressibility (unable to form a tablet by compression) and poor flow property (cannot be processed by an automated tablet press), resulting in tablets of much greater size (less dense tablet).

Micronizing drug substance particles to minimize the amount of inactive ingredients while maintaining sustained release of drugs of a high water solubility, high dose, and/or short half-life in a pharmaceutical composition is contrary to what is known in the art. The use of fine or micronized drug particles has generally been used for the opposite purpose, i.e., for a fast (not sustained) release of water-insoluble (instead of highly soluble) drugs. Micronization of a drug substance reduces its particle size thereby increasing the surface area of the solid particles, and allows for a better contact with or exposure to the surrounding liquid. A tablet containing a micronized drug substance is generally intended to increase the drug dissolution into the surrounding liquid such as gastrointestinal milieu or saliva. In addition, micronization of a drug substance has been applied almost exclusively to water-insoluble drug substances to improve their dissolution and solubility properties, leading to improved absorption and shorter onset of action. A number of drug products containing micronized water-insoluble drug substances have been marketed in the US. Tablets or capsules having the micronized drug substances are claimed to have faster action and better drug absorption than the unmicronized form. Examples include micronized fenofibrate (TRICOR® by Abbott labs), glyburide (MICRONASE® by Pfizer), tadalafil (CIALIS® by Eli Lilly), progesterone (progesterone micronized USP), griseofulvin (griseofulvin micronized, USP), etc., all of which are water-insoluble drugs.

In certain embodiments, the present invention provides pharmaceutical compositions that comprise a pharmaceutically active agent of a high water solubility, high daily dose, and/or short half-life that is micronized and dispersed in a matrix comprising a hydrophilic polymer, and contribute about or greater than 15%, 20%, 30%, 40%, 50%, or 60% of the total weight of the pharmaceutical composition.

The hydrophilic polymers useful to form a matrix in the pharmaceutical compositions of the present invention include, but are not limited to, polyvinylpyrrolidine, hydroxypropylcellulose, hydroxypropylmethyl cellulose, methyl cellulose, vinyl acetate copolymers, polysaccharides (such as alignate, chitosan, xanthum gum, pectin, guan gum, starch, dextrin, etc.), polyethylene oxide, methacrylic acid copolymers (carbomers), maleic anhydride/methyl vinyl ether copolymers, carboxymethylcellulose sodium, and derivatives and mixtures of the above-listed polymers.

In certain embodiments, the polymer is selected from hydroxypropyl cellulose, hydroxypropylmethyl cellulose (HPMC), carboxymethylcellulose sodium polyethylene oxide, methyl cellulose and methacrylic acid copolymers (carbomers), and derivatives and mixtures of the above-noted polymers. In certain embodiments, the polymer is hydroxypropylmethyl cellulose. In certain other embodiments, the polymer is hydroxypropylmethyl cellulose with a high viscosity ranging from about 4,000 mPa s to about 10,000 mPa s (measured as a 2% aqueous solution). In certain other embodiments, the high viscosity polymer is hydroxypropylmethyl cellulose, commercially available under the tradename, METHOCEL K100M Premium CR, from The Dow Chemical Company. METHOCEL K100M Premium CR EP is hypromellose 2208 that meets the requirements of the United States Pharmacopoeia XXV and European Pharmacopoeia 4th edition and is certified as Kosher. It meets apparent viscosity specification of 16922-19267 mPa·s (nominal value 18243 mPa·s) by rotation or 80000-120000 cP (nominal value 100000 cP) by the Ubbelhode method.

In certain embodiments, the polymer is HPMC of a high molecular weight. Molecular weight of a HPMC is proportional to its viscosity and is typically represented by its viscosity in a 2% aqueous solution. An "HPMC of a high molecular weight" is defined as a HPMC polymer with a nominal viscosity in mPas ranging from about 4000 to 10,000, as measured in a 2% aqueous solution.

The amount of the polymer in the dosage form generally varies from about 10% to about 50% by weight of the composition (e.g., a matrix tablet). In certain embodiments, the amount of polymers varies from about 15% to about 50%, about 15% to about 40%, about 15% to about 30%, about 15% to about 25%, about 20% to about 50%, about 20% to about 40%, about 20% to about 30%, about 25% to about 50%, or about 25% to about 40%, by weight of the composition (e.g., a matrix tablet).

The pharmaceutical composition of the invention also typically includes pharmaceutically acceptable excipients. As is well known to those skilled in the art, pharmaceutical excipients are routinely incorporated into solid dosage forms. This is done to ease the manufacturing process as well as to improve the performance of the dosage form. Common excipients include binders, diluents or bulking agents, lubricants, etc. Such excipients are routinely used in the dosage forms of this invention. Binders may be incorporated into the formulation to improve the compressibility of the bulk powder blend and thus hardness and friability of the resultant tablets. Examples of suitable binders include povidone, polyvinylpyrrolidone, xanthan gum, cellulose gums such as carboxymethylcellulose, methyl cellulose, hydroxypropylmethylcellulose, hydroxycellulose, gelatin, starch, and pregelatinized starch.

Diluents, or fillers, may be added in the compositions of the present invention to increase the mass of an individual dose to a size suitable for tablet compression. Suitable diluents include powdered sugar, calcium phosphate, calcium sulfate, microcrystalline cellulose, lactose, mannitol, kaolin, sodium chloride, dry starch, sorbitol, etc. In certain embodiments, the diluent or filler is selected from microcrystalline cellulose and lactose. In certain embodiments, the diluent or filler is microcrystalline cellulose, commercially available under the tradename AVICEL, from The FMC Biopolymer Company.

Lubricants may also be incorporated into the composition of the present invention for a variety of reasons. They reduce friction between the powder and die wall during compression and ejection. This prevents the powder from sticking to the tablet punches and facilitates its ejection from the tablet punches, etc. Examples of suitable lubricants include talc, stearic acid, vegetable oil, calcium stearate, zinc stearate, magnesium stearate, etc.

Glidants may also be incorporated into the compositions of the present invention. A glidant improves the flow characteristics of the powder. Examples of suitable glidants include talc, silicon dioxide, and cornstarch.

Other excipients that may be incorporated into the compositions of the present invention include preservatives, antioxidants, or any other excipient commonly used in the pharmaceutical industry. The amount of excipients used in the formulation will correspond to that typically used in a matrix system. The total amount of excipients, fillers and extenders, etc. varies from about 2% to about 20% by weight of the dosage form.

In certain embodiments, the pharmaceutical compositions of the present invention provide sustained release for the pharmaceutically active agents in the composition.

The term "sustained release" refers release of a drug from its dosage form (e.g., tablet) at such a rate that its blood levels are maintained within the therapeutic range (i.e., at or above minimum effective concentration (MEC)) but below toxic levels over an extended period of time (e.g., about 8, 10, 12, 14, 16, 18, 20, 22, 24 hours or greater). The term "sustained release" may be used interchangeably with "slow-release," "controlled release," or "extended release." The sustained release property of a dosage form is typically measured by an in vitro dissolution method and confirmed by an in vivo blood concentration-time profile (i.e., a pharmacokinetic profile).

The MEC of a pharmaceutically active agent of interest in a human or non-human patient may be determined using appropriate techniques known in the art (see, e.g., Grond et al., British Journal of Clinical Pharmacology 48: 254-7, 1999; and Lehmann et al., Clinical Journal of Pain 6: 212-20, 1990 for determining the MEC of tramadol in humans).

A desired specification for an in vitro dissolution is that the dosage form releases 90-100% of its drug content in a linear (0-order) or nearly linear fashion in about 18-24 hours for a once-a-day, or 10-12 hours for a twice-a-day dosage form. A desired pharmacokinetic profile is thus a blood concentration level of the drug maintained at or above its efficacy level and below its toxicity level for about 18-24 hours for a once-a-day, or 10-12 hours for a twice-a-day dosage form.

In certain embodiments, the pharmaceutical compositions of the present invention release about 90% to 100% of their pharmaceutically active agents in a linear or near linear fashion for at least about 8, 9, 10, 11, 12, 13, 14, 15, 16, 17, 18, 19, 20, 21, 22, 23, or 24 hours in an in vitro dissolution analysis as described herein. A pharmaceutically active agent is released in a "nearly linear" fashion for a specified period of time if the release rate of the agent does not change more than 20% during any hour within the specified period of time.

In certain embodiments, the pharmaceutical compositions of the present invention, upon oral administration to a human or non-human patient in need thereof, has an in vitro dissolution rate measured by the Ph. Eur. Paddle method at 100 rpm in 900 ml 0.1 N hydrochloric acid at 37° C. and using UV detection at 270 nm or by the method as described in Example 2 or 11 from about 5% to about 40% of the pharmaceutically active agent released after 2 hours, from about 15% to about 55% of the pharmaceutically active agent released after 4 hours, from about 40% to about 80% of the pharmaceutically active agent released after 8 hours, from about 60% to about 95% of the pharmaceutically active agent released after 12 hours, and from about 70% to about 100% of the pharmaceutically active agent released after 18 hours by weight.

In certain embodiments, the pharmaceutical compositions of the present invention, upon oral administration to a human or non-human patient in need thereof, has an in vitro dissolution rate measured by one of the methods described above from about 10% to about 30% of the pharmaceutically active agent released after 2 hours, from about 25% to about 45% of the pharmaceutically active agent released after 4 hours, from about 50% to about 70% of the pharmaceutically active agent released after 8 hours, from about 70% to about 90% of the pharmaceutically active agent released after 12 hours, and from about 80% to about 100% of the pharmaceutically active agent released after 18 hours by weight.

In some of the above-noted embodiments related to in vitro dissolution rate, the pharmaceutical compositions are in the form of a matrix tablet and may be orally administered to a patient in need thereof as either an intact or crushed tablet.

In certain embodiments, the pharmaceutical compositions (e.g., matrix tablets) of the present invention, upon oral administration to a human or non-human patient in need thereof, provides sustained release of the pharmaceutically active agents in the compositions for at least about 8, 9, 10, 11, 12, 13, 14, 15, 16, 17, 18, 19, 20, 21, 22, 23, 24, 36, 48, 72, 96, 120, 144, or 168 hours.

In certain embodiments, the pharmaceutical compositions are in the form of matrix tablets suitable for one-a-day or twice-a-day administration to a human or non-human patient. In certain other embodiments, the pharmaceutical compositions are in the form of matrix tablets suitable for administration to a human or non-human patient no more than once per two, three, four, five, six, or seven days. In certain embodiments, the patient is a cat, the pharmaceutical compositions are in the form of matrix tablets containing tramadol and suitable for administration for oral administration once per three days or once per week.

In certain embodiments, the pharmaceutical compositions of the present invention, upon oral administration to a human or non-human patient in need thereof, produce a pharmacokinetic profile with a $T_{max}$ of about 1 to 18 hours, such as about 1 to 16, 1 to 14, 1 to 12, 1 to 10, 1 to 8, 1 to 6, 2 to 16, 2 to 14, 2 to 12, 2 to 10, 2 to 8, 2 to 6,4 to 16, 4 to 14, 4 to 12, 4 to 10, 4 to 8, or 4 to 6 hours.

The term "$T_{max}$" refers to the time for the plasma concentration of a pharmaceutically active agent to reach its maximum value after a pharmaceutical composition comprising the pharmaceutically active agent is administered to a patient.

In certain embodiments, the pharmaceutical compositions of the present invention, upon oral administration to a human or non-human patient in need thereof, produce a pharmacokinetic profile with a $W_{50}$ value in the range of about 6 to 18 hours, such as about 8 to 16, 8 to 14, 8 to 12, or 8 to 10 hours.

The term "$W_{50}$" refers to the width of a pharmacokinetic profile at 50% $C_{max}$, that is, the duration over which the plasma concentrations are equal to or greater than 50% of the peak plasma concentration (i.e., $C_{max}$).

In certain embodiments, the pharmaceutical compositions of the present invention, upon oral administration to a human or non-human patient in need thereof, produce an Area Under the Curve (AUC) (0 to infinity) (plasma concentration versus time) of the pharmaceutically active agent at least about 50%, 100%, 150%, 200%, or 250% higher than the AUC (0 to infinity) provided by an immediate release formulation containing the same amount of the pharmaceutically active agent.

The term "Area Under the Curve (AUC)" refers to a parameter determined from the graphical presentation of an actual or theoretical plasma profile (concentration verse time) that represents the area under the curve of such a profile. The term "AUC (0 to infinity)" refers to the total area under the curve of a plasma concentration versus time profile from the time of administration to infinity. AUC may be measured or determined by appropriate methods known in the art. One exemplary method is described in KuKanich & Papich (J. Vet. Pharmacol. Therap. 27, 239-46, 2004).

An "immediate release formulation" (or "immediate release form", or the like) of a drug refers to a formulation that releases at least 80% of the drug within one hour measured by an in vitro dissolution method, such as those described herein.

In certain embodiments, the pharmaceutical compositions of the present invention comprise tramadol, and upon oral administration in a dog, provide an AUC (0 to infinity) (plasma concentration versus time) of tramadol about or greater than 2, 4, or 6 µg hr/mL. In certain embodiments, such pharmaceutical compositions, upon oral administration in a dog, further provide a $C_{max}$ of tradamol about or less than 10 µg/mL.

In certain embodiments, the pharmaceutical compositions of the present invention comprise tramadol, and upon oral administration in a dog, provide an AUC (0 to infinity) (plasma concentration versus time) of the active metabolite of tramadol, M1 (O-desmethyltramadol), about or greater than 0.2, 0.4, 0.6, 0.8, 1.0, or 1.2 µg hr/mL. In certain embodiments, such pharmaceutical compositions, upon oral administration in a dog, further provide a $C_{max}$ of M1 about or less than 2 µg/mL.

In certain embodiments, the composition of the present invention, upon oral administration to a patient in need thereof, provides a plasma concentration at or above a therapeutically effective concentration for a period of time that is at least about 100%, 150%, 200%, or 250% longer than an immediate release formulation containing the same amount of the pharmaceutically active agent.

The pharmaceutical compositions (e.g., matrix tablets) are generally prepared using standard techniques well known in the art. In certain embodiments, they may be prepared by (a) micronizing a drug of a high water solubility, short half-life and high dose, as needed, (b) selecting drug particles having an upper size limit of about or less than 210 micron (70 mesh) and a lower limit of about or greater than 63 micron (230 mesh), such as an upper size limit of about or less than 125 micron (120 mesh) and a lower size limit of about or greater than 74 micron (200 mesh), (c) optionally passing a hydrophilic polymer and excipients through a 70 mesh sieve, (d) dry blending the drug with the hydrophilic polymer, a diluent, a binder, and/or one or more other excipients to uniformity, (e) optionally lubricating the powder blend with a lubricant/glidant, (f) compressing the resulting mixture into tablets (e.g., those of hardness of about 10 to 20 kp using, for example, a conventional tablet press), and (g) optionally coating the tablets, for example, using a spray coater or a fluid bed coater.

In certain embodiments, a matrix tablet of this invention may be prepared by: (a) Micronizing a drug of a high water solubility, short half-life and high dose using a FITZMILL® Comminutor by Fitzpatrick Corp. (Elmhurst, Ill.). The FITZMILL® Comminutor can be configured for comminution to a specific particle range, or fine grinding applications. The micronizing step is applied to only coarse drug substances with particle size exceeding the upper limit of the desired size range, i.e., 210 micron (70 mesh). Most commercially available drug substances are regarded "coarse" for this invention and thus require size reduction. For drug substances with a fine particle size to begin with, this step may not be necessary.

(b) Sieving the micronized or unmicronized drug substance and selecting the fraction with an upper size limit of about or less than 210 micron (70 mesh) and a lower limit of about or greater than 63 micron (230 mesh), such as an upper limit of about or less than 177 micron (80 mesh) and a lower limit of about or greater than 74 micron (200 mesh), an upper limit of about or less than 149 micron (100 mesh) and a lower limit of about or greater than 74 micron (200 mesh), and an upper limit of about or less than 125 micron (120 mesh) and a lower limit of about or greater than 74 micron (200 mesh). The sieving can be done using conventional standard sieves and sieving equipment, such as a Russel Model 16300 Portable Sieve.

(c) Additionally, passing the hydrophilic polymer and all excipients individually or combined through a 70 mesh sieve.

(d) Combining and dry blending a mixture of the sieved drug substance from about 50 weight percent to about 80 weight percent, a hydrophilic polymer from about 10 weight percent to about 40 weight percent, and an excipient(s) (filler and/or binder) from about 2 weight percent to about 20 weight percent, to obtain a uniform powder blend. The dry blending can be done using a conventional powder blender such as a Patterson-Kelly V-blender. A typical blending time is about 15 to 30 minutes.

(e) Adding to the powder blend produced in step (d) a lubricant and/or glidant of about 1 weight percent to about 3 weight percent and blending for 1-5 minutes, preferable about 2 minutes.

(f) Compressing the powder blend from step (e) into tablets with hardness of about 10 to 20 kp using a conventional tablet press such as a Colton rotary press. The tablet weight may vary from about 400 to 2000 mg. Any tablet shape that is easy swallowed is desired. A score or certain trademark feature may also be added to the tablet.

(g) Optionally, spray coating the tablets with film coatings, release-controlling coatings or enteric coating for the purpose of taste masking, easing swallow ability, extended release or acid protection, etc. The coating may be colored with a pharmaceutically accepted dye. The process may be accomplished using a conventional spray coater (e.g., a VECTOR HI-COATER) or a fluidized bed processor (e.g., a GLATT MODEL GPCG-5 COATER).

In certain embodiments, the tablets are processed by a direct compression method. Direct compression is a simplest process of making tablets where all tablet components are dry mixed to form a uniform blend and then directly compressed into tablets. It requires the tablet component blend to possess adequate flow property and compressibility. Direct compression eliminates other processing steps such as granulation, which is required for a tablet component blend that does not have suitable flow or compression property.

The coating liquid generally comprises film forming polymers such as hydroxypropyl cellulose, hydroxypropylmethyl cellulose, cellulose esters or ethers (such as cellulose acetate or ethylcellulose), an acrylic polymer or a mixture of polymers. The coating solution is generally an aqueous solution or an organic solvent further comprising propylene glycol, sorbitan monoleate, sorbic acid, fillers such as titanium dioxide, a pharmaceutically acceptable dye.

An exemplary coating system for taste masking, easing swallow ability, and/or extended release comprises an aqueous dispersion of ethyl cellulose, oleic acid, ammonium hydroxide and water (under the tradename of Surelease E-7-19010 by Colorcon) and a polyethylene glycol aqueous solution (under the tradename Opadry II by Colorcon). An exemplary coating system is a mixture of about 20-50% Surelease E-7-19010), about 0.5-5% Opadry, and water.

In certain embodiments, the matrix tablets of the present invention comprise a coating layer that controls the release of the drug in the matrix tablets (referred to as a "release controlling coating," "release controlling layer," or "release controlling coating layer"). A coating controls the release of a drug in a matrix tablet if the release of the drug over time in the matrix tablet with the coating is statistically significantly different from that in the matrix tablet without the coating. In certain embodiments, the coating prolongs the release of the drug in the matrix tablet. For example, the coating may increase the time the effective plasma concentration of the drug in a patient after administered with the matrix tablet for about 1, 2, 3, 4, or 5 hours.

In certain other embodiments, the matrix tablets of the present invention comprise a coating layer that does not control the release of the drug in the matrix tablets. Such a coating may have one or more other properties, such as taste masking or facilitating swallow.

In certain embodiments, the matrix tablet of the present invention is of an oval shape with a single score perpendicular to the long axis of the tablet. Such a design facilitates the fragmentation of the matrix tablets and minimizes the disruption of the integrity of the resulting tablet fragments.

An exemplary matrix tablet composition for the extended release of the drug of a high-solubility, short half-life and high dose comprises: from about 55 weight percent to about 75 weight percent of a micronized tramadol HCl; from about 20 weight percent to about 25 weight percent of hydroxypropyl methylcellulose (METHOCEL™ K100M Premium CR); from about 2 weight percent to about 20 weight percent of microcrystalline cellulose (AVICEL PH102); from about 0.5 weight percent to about 2 weight percent of magnesium stearate, USP; and from about 1 weight percent to about 3 weight percent of a film coating comprising Surelease E-7-19010 and Opadry II.

Another exemplary matrix composition in a form of an orally deliverable SR tablet comprising tramadol hydrochloride having an upper size limit of about or less than 125 micron (120 mesh) and a lower size limit of about or greater than 74 micron (200 mesh) in an amount of about 75, 90, 100, 180, 200, 300, 400, 500, 600, 700, 800, 900, or 1000 mg, dispersed in a matrix comprising: (a) HPMC of a high molecular weight (e.g., METHOCEL™ K100M by Dow Chemical) in an amount of about 20% to about 30% by weight of the tablet, (b) a microcrystalline cellulose having a particle size of not greater than 210 micron, in an amount of about 10% to about 20% by weight of the tablet, (c) a tableting lubricant in an amount of about 1% to about 3% by weight of the tablet, and (d) optionally a film coating (e.g., a film coating comprising Surelease E-7-19010 and Opadry II) of about 1 weight percent to about 3 weight percent of the tablet. In this exemplary matrix composition, the tramadol hydrochloride may contribute about 44% to about 69% of the total weight of the tablet.

In another aspect, the present invention provides a pharmaceutical composition in the form of an orally deliverable tablet comprising tramadol hydrochloride having an upper size limit of about or less than 125 micron (120 mesh) and a lower size limit of about or greater than 74 micron (200 mesh) in an amount of about 150 mg to about 500 mg (e.g., about 150, 200, 250, 300, 350, 400, 450, or 500 mg), dispersed in a matrix comprising (a) HPMC of a high molecular weight (e.g., METHOCEL™ K100M by Dow Chemical) in an amount of about 20% to about 40% by weight of the tablet, (b) a microcrystalline cellulose having a particle size of about or less than 210 micron, in an amount of about 10% to about 30% by weight of the tablet, (c) a tableting lubricant in an amount of about 1% to about 3% by weight of the tablet, and (d) optionally a film coating (e.g., a film coating comprising Surelease E-7-19010 and Opadry II) of about 1 weight percent to about 3 weight percent of the tablet. In this exemplary matrix composition, the tramadol hydrochloride may contribute about 27% to about 69% of the total weight of the tablet.

Another exemplary matrix composition in a form of an orally deliverable SR tablet comprises glucosamine HCl or another salt such as N-butyryl glucosamine having an upper size limit of about or less than 125 micron (120 mesh) and a lower size limit of about or greater than 74 micron (200 mesh) in an amount of about 100, 200, 300, 400, 500, 600, 700, 800, 900, 1000, 1100, 1200, 1300, 1400, or 1500 mg, dispersed in a matrix comprising: (a) HPMC of a high molecular weight (e.g., METHOCEL™ K100M by Dow Chemical) in an amount of about 20% to about 30% by weight of the tablet, (b) a binder having a particle size of about or less than 210 micron, in an amount of about 2% to about 20% by weight of the tablet, (c) a tableting lubricant in an amount of about 1% to about 3% by weight of the tablet, and (d) optionally a film coating (e.g., a film coating comprising Surelease E-7-19010 and Opadry II) of about 1 weight percent to about 3 weight percent of the tablet. In this exemplary matrix composition, glucosamine HCl or another salt such as N-butyryl glucosamine may contribute about 50% to about 77% of the total weight of the matrix composition.

Yet another exemplary matrix composition in a form of an orally deliverable SR tablet comprises glucosamine HCl having an upper size limit of about or less than 125 micron (120 mesh) and a lower size limit of about or greater than 74 micron (200 mesh) in an amount of about 100, 200, 300, 400, 500, 600, 700, 800, 900, 1000, 1100, 1200, 1300, 1400 or 1500 mg, and chondroitin sulfate having an upper size limit of about or less than 125 micron (120 mesh) and a lower size limit of about or greater than 74 micron (200 mesh) in an amount of about 100, 200, 300, 400, 500, 600, 700, 800, 900, 1000, 1100, 1200, 1300, 1400 or 1500 mg, dispersed in a matrix comprising: (a) HPMC of a high molecular weight (e.g., METHOCEL™ K100M by Dow Chemical) in an amount of about 20% to about 30% by weight of the tablet, (b) a binder having a particle size of about or less than 210 micron, in an amount of about 2% to about 20% by weight of the tablet, (c) a tableting lubricant in an amount of about 1% to about 3% by weight of the tablet, and (d) optionally a film coating (e.g., a film coating comprising Surelease E-7-19010 and Opadry II) of about 1 weight percent to about 3 weight percent of the tablet. In this exemplary matrix composition, glucosamine HCl and chondroitin sulfate together may contribute about 50% to about 77% of the total weight of the matrix composition.

Yet another exemplary matrix composition in a form of an orally deliverable SR tablet comprises gabapentin having an upper size limit of about or less than 125 micron (120 mesh) and a lower size limit of about or greater than 74 micron (200 mesh) in an amount of about 100, 200, 300, 400, 500, 600, 700, 800, 900, 1000, 1100, 1200, 1300, 1400 or 1500 mg, dispersed in a matrix comprising: (a) HPMC of a high molecular weight (e.g., METHOCEL™ K100M by Dow Chemical) in an amount of about 20% to about 30% by weight of the tablet, (b) a binder having a particle size of about or less than 210 micron, in an amount of about 2% to about 20% by weight of the tablet, (c) a tableting lubricant in an amount of about 1% to about 3% by weight of the tablet, and (d) optionally a film coating (e.g., a film coating comprising Surelease E-7-19010 and Opadry II) of about 1 weight percent to about 3 weight percent of the tablet. In this exemplary matrix composition, gabapentin may contribute about 50% to about 77% of the total weight of the matrix composition.

A further exemplary matrix composition in a form of an orally deliverable SR tablet comprises metformin hydrochloride having an upper size limit of about or less than 125 micron (120 mesh) and a lower size limit of about or greater than 74 micron (200 mesh) in an amount of about 100, 200, 300, 400, 500, 600, 700, 800, 900, 1000, 1100, 1200, 1300, 1400 or 1500 mg, dispersed in a matrix comprising: (a) HPMC of a high molecular weight (e.g., METHOCEL™ K100M by Dow Chemical) in an amount of about 20% to about 30% by weight of the tablet, (b) a binder having a particle size of about or less than 210 micron, in an amount of about 2% to about 20% by weight of the tablet, (c) a tableting lubricant in an amount of about 1% to about 3% by weight of the tablet, and (d) optionally a film coating (e.g., a film coating comprising Surelease E-7-19010 and Opadry II) of about 1 weight percent to about 3 weight percent of the tablet. In this exemplary matrix composition, metformin hydrochloride may contribute about 44% to about 77% of the total weight of the matrix composition.

A further exemplary matrix composition in a form of an orally deliverable SR tablet comprises acetaminophen having an upper size limit of about or less than 125 micron (120 mesh) and a lower size limit of about or greater than 74 micron (200 mesh) in an amount of about 100, 200, 300, 400, 500, 600, 700, 800, 900, 1000, 1100, 1200, 1300, 1400 or 1500 mg, dispersed in a matrix comprising: (a) HPMC of a high molecular weight (e.g., METHOCEL™ K100M by Dow Chemical) in an amount of about 20% to about 30% by weight of the tablet, (b) a microcrystalline cellulose having a particle size of about or less than 210 micron, in an amount of about 10% to about 20% by weight of the tablet, (c) a tableting lubricant in an amount of about 1% to about 3% by weight of the tablet, and optionally (d) a film coating (e.g., a film coating comprising Surelease E-7-19010 and Opadry II) of about 1 weight percent to about 3 weight percent of the tablet. In this exemplary matrix composition, acetaminophen may contribute about 44% to about 69% of the total weight of the matrix composition.

In one aspect, the present invention provides methods for using the pharmaceutical compositions described herein. Such pharmaceutical compositions may be used for treating or preventing (i.e., reducing the risk of) diseases or disorders that the pharmaceutically active agents in the compositions are suitable for treating or preventing.

In certain embodiments, the present invention provides a method for reducing pain comprising administering orally to a patient in need thereof a pharmaceutical composition as described herein that comprises an effective amount of tramadol, tramadol HCl or another pharmaceutically acceptable salt.

In certain embodiments, the present invention provides a method for reducing joint discomfort or increasing joint flexibility comprising administering orally to a patient in need thereof a pharmaceutical composition as described herein that comprises an effective amount of glucosamine, glucosamine HCl or another pharmaceutically acceptable salt.

In certain embodiments, the present invention provides a method for reducing joint discomfort or increasing joint flexibility comprising administering orally to a patient in need thereof a pharmaceutical composition as described herein that comprises an effective amount of glucosamine HCl and chondroitin sulfate.

In certain embodiments, the present invention provides a method for reducing pain or fever that comprises administering orally to a patient in need thereof a pharmaceutical composition as described herein comprising an effective amount of acetaminophen.

In certain embodiments, the present invention provides a method for treating or preventing (i.e., reducing the risk of) seizure or reducing neuropathic pain that comprises administering orally to a patient in need thereof a pharmaceutical composition as described herein comprising an effective amount of gabapentin.

In certain embodiments, the present invention provides a method for lowering blood sugar level comprising administering orally to a patient in need thereof a pharmaceutical composition as described herein that comprises an effective amount of metformin hydrochloride.

Patients in need of treatment or prevention of a disease or disorder include both human patients (e.g., adult human patients) and non-human patients (e.g., dogs, cats, horses, and other pets or farm animals). As described above, the matrix tablets of the present invention are especially suitable for animal use because such tablets, unlike other tablets in which controlled release of drugs depend on their intact coating, provide controlled release of drugs even after being chewed, fragmented or crushed.

An "effective amount" refers to the amount of a pharmaceutically active agent effective in treating or preventing a disease or disorder. Such amount may be determined by appropriate methods known in the art. For instance, a sufficient amount of an analgesic or analgesics (such as tramadol and acetaminophen) in a pharmaceutical composition of the present invention may be determined using various methods for measuring analgesia, such as those described in U.S. Patent Application Publication No. 20050089558, Collier et al., Br. J. Pharmacol. 32: 295, 1968; D'Amour et al., J. Pharmacol. Exp. Ther. 72: 74, 1941; and Hargreaves et al., Pain 32: 77, 1988.

To exemplify the results achieved using the sustained release compositions of the present invention, the following examples are provided without any intent to limit the scope of the instant invention to the discussion therein. All parts and percentages are by weight unless otherwise indicated.

EXAMPLES

Example 1

Composition and Method for Preparing Tramadol SR Matrix Tablets

Herein below, describes components, composition, manufacturing process, test and specification of a tramadol HCl sustained release tablets prepared by the methods disclosed in this invention. Tramadol HCl is "freely soluble" in water according to the USP definition. Due to its short half-life, an SR tablet of tramadol is desired for pain management including pains associated with osteoarthritis in dogs and humans.

Components and Composition

The tramadol sustained release tablets presented in this example are coated matrix tablets of this invention. The components and compositions of the uncoated tablet and the coating are listed separately in the tables below:

Uncoated Matrix Tablet

| Component | % w/w | Mg per tablet | Brand and Manufacturer |
|---|---|---|---|
| Tramadol HCl, micronized* | 60.0 | 600 | DAI-ICHI KARKARIA |
| Hydroxypropyl Methylcellulose, USP | 22.4 | 224 | Methocel K100M Prem CR by Dow Chemical |

-continued

| Component | % w/w | Mg per tablet | Brand and Manufacturer |
|---|---|---|---|
| Microcrystalline Cellulose, NF | 15.6 | 156 | Avicel PH-102 by FMC BioPolymer |
| Magnesium Stearate, NF | 2.0 | 20 | Witco Corporation |
| Total | 100 | 1000 | |

*The particle size of this material is rated at 120 mesh, i.e., 90% of the tramadol HCl drug substance can pass through a 120 mesh sieve (121 micron).

Coating Dispersion

| Component | % w/w | Grade | Brand and Manufacturer |
|---|---|---|---|
| An aqueous dispersion containing ethyl cellulose, oleic acid, ammonium hydroxide and water | 34.0 | NF | Surelease E-7-19010 by Colorcon |
| A solution containing polyethylene glycol | 1.5 | NF | Opadry II by Colorcon |
| DI Water | 64.5 | | E-Pure by Barnstead |
| Coating weight | 2% of the weight of an uncoated tablet | | |

Average uncoated tablet weight is 1000 mg and average coating weight is 20 mg per tablet.

The tablets are in an oval shape with a bisecting score on one side.

The uncoated tablets are monolithic and non-disintegrating.

The in vitro release of tramadol is insensitive to pH of the dissolution medium due to lack of ionizable and soluble excipients in the formulation, and insensitive to speed of agitation because of the non-disintegrating and slow erosion nature of the tablets.

The tablets are coated to further control the drug release (FIG. 1) and to improve taste and ease of swallow of the tablets. The coating is intended (1) to suppress the initial burst release of the uncoated tablets, (2) to provide an improved zero-order release, (3) to extend the release to about 20-24 hours (from the 12-16 hr of the uncoated tablets), (4) for taste masking (tramadol HCl tastes very salty and somewhat bitter), (5) to serve as a protective layer, and finally (6) for easy swallow.

The uncoated tablets are likely to be twice-a-day tablets, while the coated tablets may be for once-a-day use.

The uncoated tablets are produced by a direct compression method using a rotary tablet press.

The tablets are spray coated in a pan coater.

Manufacturing Process

The tablets of this example may be manufactured following the general steps as listed below:

Micronizing

1. Charge a coarse tramadol HCl drug substance into a FitzMill Model DAS06 Comminutor. Grind the powder for 10-60 minutes to reduce particle size.
2. Collect the product and pass through a 120 mesh sieve. Collect the fraction that passes through the 120 mesh sieve.
3. Determine the % of extra-fine particles (i.e., <74 micron) present in the collected fraction, if the wt % extra-fine particle exceeds 10% of the total weight, sieve the fraction through a 200 mesh sieve to remove the extra-fine particles.

Tableting

1. Weigh out HPMC (METHOCEL K100M Premium CR), microcrystalline cellulose (AVICEL PH102) and tramadol HCl (micronized), transfer into a V-blender, mix for 2-10 minutes.
2. Pass the mixture through a 70-mesh sieve.
3. Charge the mixture into the V-blender again and mix for 20 minutes to form a uniform powder mixture.
4. Add magnesium stearate, mix for 0.5-2 minutes.
5. Compress into oval shaped tablets of appropriate weight and hardness (10-20 kp).
6. Vacuum dedust the tablets.
7. Store the tablets in appropriated container for coating process.

Coating

1. Mix Opadry II and Surelease dispersion to form the final coating dispersion.
2. Charge an appropriate number of tablets into a coating pan and start coating using the following approximate conditions:
   Pan rotation: 10-50 RPM
   Liquid spray rate: 5-30 mL/min
   Dry air temperature: 40-70° C.
3. The final weight gain is 2.0±0.2% based on the average uncoated tablet weight.

Specification

The tablets of this example may be tested against the following quality specifications:

| Test | Method | Specification |
|---|---|---|
| Appearance | Visual | A white or off-while and oval shape tablet without any chip, defeat, or layers |
| In vitro dissolution | USP dissolution apparatus II | Meet the requirement |
| Identification | HPLC | Conforms to standard |
| Uniformity of dosage units | HPLC | Meet the requirement |
| Assay | HPLC | 90 to 110% label claim |

Example 2

Effects of Drug Particle Size on In Vitro Dissolution Rate of Tramadol SR Matrix Tablets This example exhibits the significant effect of drug particle size on in vitro dissolution rate from the tablets prepared according to this invention. In addition, this example shows that fine or micronized drug substance particles, in the size specification defined in this disclosure, are required to provide the sustained or extended release of a drug of high-solubility, short half-life and high dose.

Multiple lots of tramadol hydrochloride drug substances of varying particle size (Table below) were used to prepare the matrix tablets using the method described in Example 1.

| Particle size of tramadol HCl | Manufacture and lot number | Upper particle size limit* | Note |
|---|---|---|---|
| "Coarse" | Degussa, lot 0041194237 | >400 micron | This lot was difficult to process - extra compression forces were needed to obtain tablets that meet the hardness specification, but it failed to meet the dissolution specification |

-continued

| Particle size of tramadol HCl | Manufacture and lot number | Upper particle size limit* | Note |
|---|---|---|---|
| "Micronized" | Dai-Ichi Karkaria, Ltd. lot TDL/M/03/04004 | 210 micron | This lot was processed to form tablets that meet the hardness and dissolution specifications, using the method disclosed in this application |
| A fine particle fraction collected by sieving a coarse starting material through a 120 mesh sieve | Dai Ichi Karkaraia Ltd., lot DKM04030 | 125 micron | This lot was processed to form tablets that meet the hardness and dissolution specifications, using the method disclosed in this application |
| "Extra-fine" | Chemagis, lot 3TRMDN0F505 | 80 micron | This lot was very fluffy and had a poor flow property and could not processed to form tablets of the target size or hardness, using the method disclosed in this application |

*Upper particle size limit: a value by which 95% of the particles are below in size.

An in vitro dissolution test was carried for the tablets prepared according to this invention using a standard UPS dissolution apparatus II (Paddle). The method is detailed as follow:

| | |
|---|---|
| APPARATUS: | USP dissolution apparatus II (Paddle) |
| Medium: | USP Simulated gastric fluid (without enzymes) |
| Medium volume: | 1000 mL |
| Temperature: | 37° C. |
| Stir: | 50 RPM |
| Sample volume: | 1 mL (without replenishment with fresh medium). Each sample was filtered through a 10-micron filter prior to filling into HPLC vial. |
| Sampling time: | 0.25, 0.5, 0.75, 1, 2, 3, 6, 12, 18 and 24 hours |
| Tablet sinker: | A metal wire sinker with an approximate diameter of 0.8 mm and 1 g weight was used to coil around each tablet and to hold a tablet to the bottom of the vessel to prevent floating or movement during the stirring. |
| Sample analysis: | HPLC |
| Date normalization: | After 24 hours, the remaining tablet mass (a soft gel) was homogenized in the medium using a mechanical mixer to form a uniform dispersion, which was then filtered through the 10-micron filter and analyzed by HPLC as the "100% release" sample. The in vitro release (%) values in all previous samples (0.25-24 hr) were normalized based on the "100% release" using the following equation: % release = 100* (tramadol conc. in a previous sample)/(tramadol conc. in the "100% release sample") |

The concentration of tramadol in the medium samples were analyzed using a reversed phase HPLC method with the following conditions:

| | |
|---|---|
| System: | An HPLC system capable of performing binary gradient elution and UV detection |
| Column: | Luna C18 5μ, 4.6 × 250 mm, by Phenomenex Part # 00G-4041-E0 |
| Mobile Phase A: | 0.1% v/v trifluroacetic acid in water, 0.8 micron filtered |
| Mobile Phase B: | 0.1% v/v trifluroacetic acid in acetonitrile, 0.8 micron filtered |
| Column temp: | 40° C. |
| Injection: | 5 μL |
| UV Detection: | 270 nm |
| Run time: | 5 min |
| Elution: | Isocratic at 65% (v/v) Mobile Phase A and 35% (v/v) Mobile Phase B |

Figure 2:
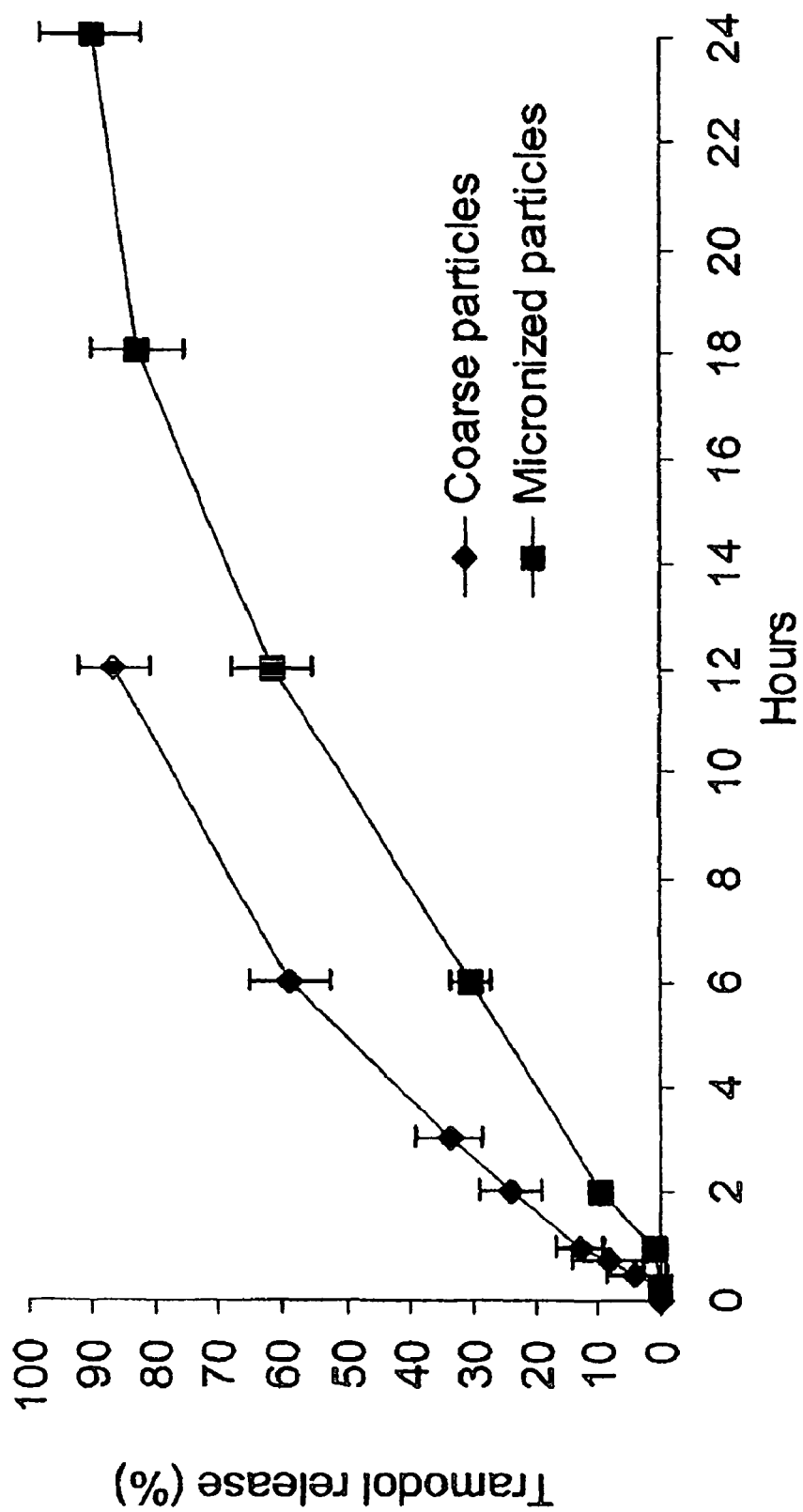
FIG. 2 is a graph that compares the in vitro release rate of tramadol hydrochloride from a coated matrix tablet composition prepared according to Example 1 of the present application using (a) "micronized" particles of tramadol HCl (Dai-lchi Karkaria, Ltd. lot TDL/M/03/04004), with (b) a "coarse" tramadol HCl substance (Degussa, lot 0041194237). The tablets made with the "coarse" particles failed to meet the dissolution specification, i.e., coated tablets to release 80-100% of tramadol in about 18-24 hours.

The in vitro dissolution results from these tablets are depicted in FIG. 2. It is apparent that only the tablets made with micronized particles of tramadol hydrochloride drug substances in the specified particle size range were able to provide the sustained release characteristics desired specification (i.e., coated tablets to release about 80-100% in about 18-24 hours). Tablets prepared with coarse drug particles exhibited a significantly fast dissolution rate and failed to meet the sustained release requirement set forth for these tablets. The extra-fine tramadol hydrochloride did not flow and compress properly using the method described in this application. The tablets formed were very soft and fragile and could not be coated due to a very high friability.

Example 3

Figure 3A:
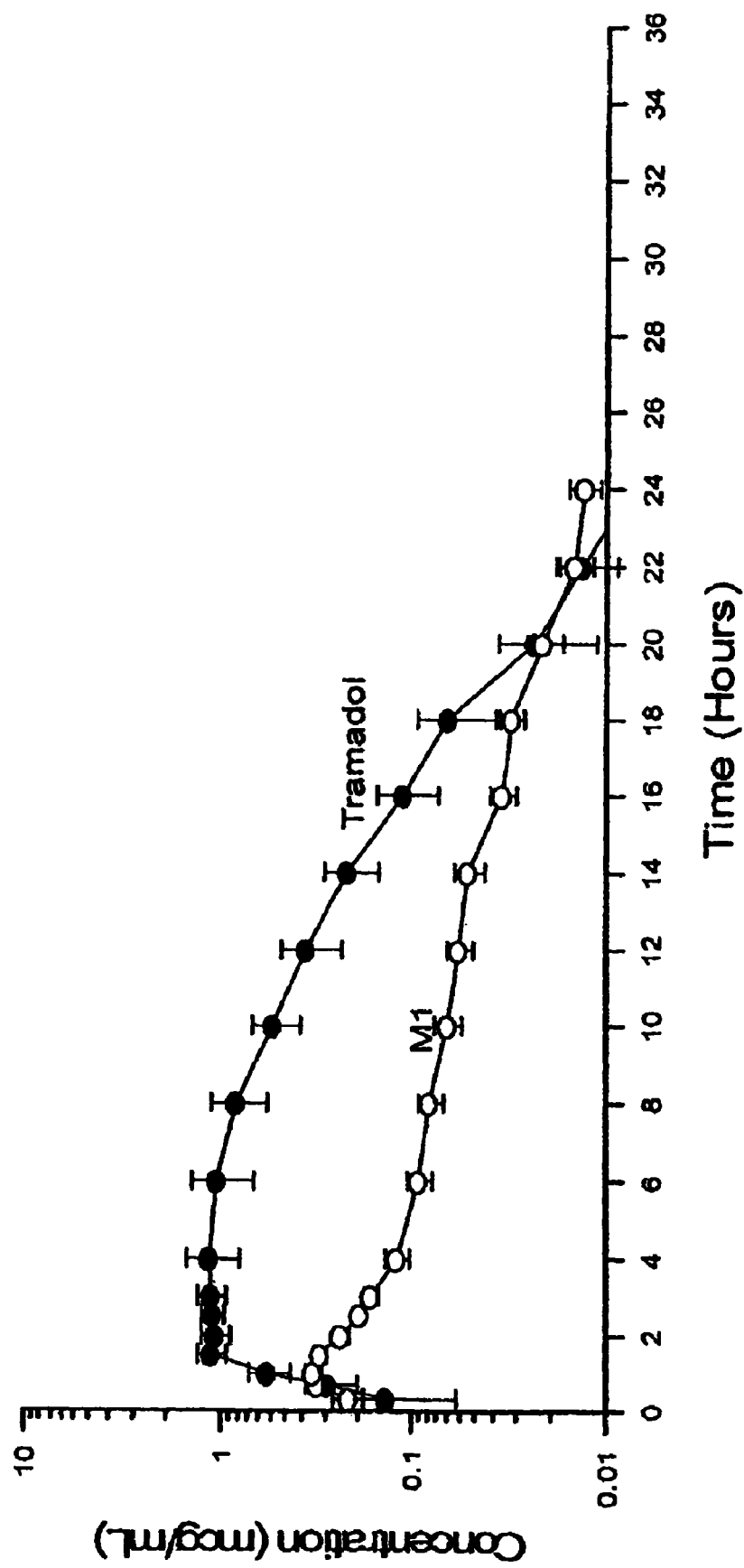
FIGS. 3A and 3B are graphs that depict the in vivo release rate in dogs of tramadol hydrochloride from a SR tramadol HCl matrix tablet prepared according to Example 3 of the present application using fine particles of tramadol HCl.
Figure 3B:
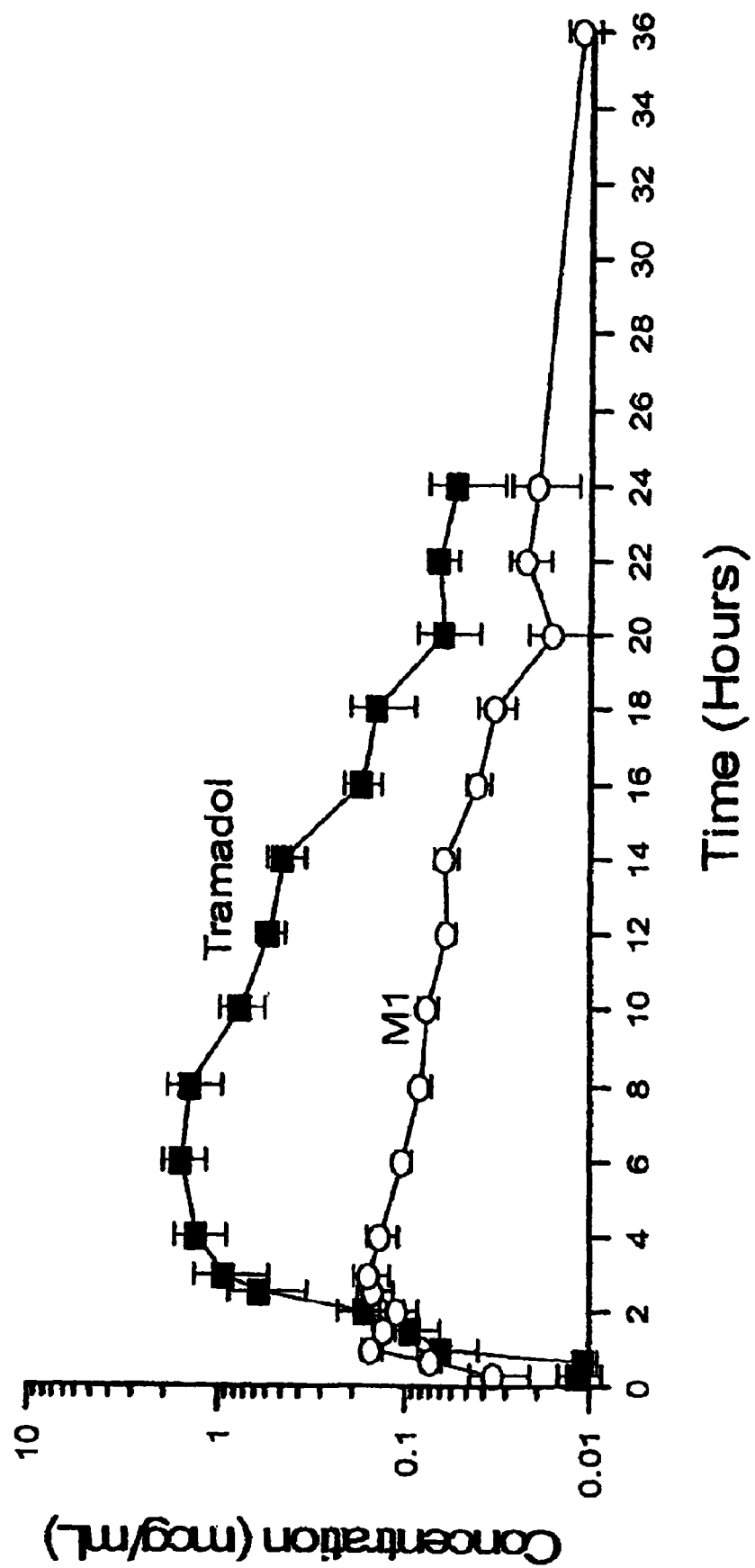

In Vivo Pharmacokinetic Analysis of Coated and Uncoated Tramadol SR Matrix Tablets The tramadol HCl SR tablets prepared according to Example 1 (i.e., 600 mg tablets) were administered orally to fasted beagle dogs of an approximate body weight of 10 kg. In Group No. 1 (6 dogs, n=6), each 600 mg uncoated SR tramadol HCl tablet was broken at the scored line and a half tablet (containing 300 mg tramadol HCl) was given to each dog. In Group No. 2 (6 dogs, n=6), each 600 mg coated SR tramadol HCl tablet was broken at the scored line and a half tablet (containing 300 mg tramadol HCl) was given to each dog. Blood samples were taken at 20 m, 40 m, 60 m, 1.5 h, 2 h, 2.5 h, 3 h, 4 h, 6 h, 8 h, 10 h, 12 h, 14 h, 16 h, 18 h, 20 h, 22 h, 24 h and 36 h and analyzed by high performance liquid chromatography (HPLC) for concentration of tramadol and its active metabolite M1 (O-desmethyltramadol). The blood concentration profiles are shown in FIGS. 3A and 3B.

The pharmacokinetic parameters determined are listed in the table below:

| | | Dog_Number | | | | | | | |
|---|---|---|---|---|---|---|---|---|---|
| Paramaeter | Units | 206 | 207 | 209 | 215 | 222 | 224 | Mean | Std. Dev. |
| Group 1: M1 Pharmacokinetics | | | | | | | | | |
| Rsq | | 0.884 | 0.911 | 0.9534 | 0.971 | 0.9423 | 0.9338 | 0.933 | 0.031 |
| Lambda_z | 1/hr | 0.1664 | 0.1638 | 0.0804 | 0.1379 | 0.0954 | 0.141 | 0.131 | 0.036 |
| Half-life | hr | 4.1649 | 4.2308 | 8.6257 | 5.0249 | 7.2687 | 4.9146 | 5.705 | 1.823 |
| Tmax | hr | 1 | 1 | 1 | 0.67 | 1 | 1.5 | 1.028 | 0.266 |

-continued

| | | | | | | | | Mean | Std. Dev. |
|---|---|---|---|---|---|---|---|---|---|
| Cmax | ug/mL | 0.3597 | 0.3843 | 0.3512 | 0.3363 | 0.4052 | 0.351 | 0.365 | 0.025 |
| Tlast | hr | 24 | 24 | 24 | 24 | 24 | 16 | 22.667 | 3.266 |
| Clast | ug/mL | 0.0048 | 0.0083 | 0.0129 | 0.0221 | 0.0167 | 0.009 | 0.012 | 0.006 |
| AUC(0_to_Clast) | hr * ug/mL | 1.8493 | 2.2478 | 1.4644 | 2.1028 | 2.2874 | 1.0944 | 1.841 | 0.476 |
| AUC(0_to_infinity) | hr * ug/mL | 1.8854 | 2.3048 | 1.6382 | 2.1874 | 2.5262 | 1.1667 | 1.951 | 0.496 |
| AUC_(%_extrap.) | % | 1.9161 | 2.4719 | 10.6114 | 3.8689 | 9.4497 | 6.1947 | 5.752 | 3.647 |
| Vz_F_pred | mL/kg | 95608.76 | 79448.84 | 227882.5 | 99425.41 | 124535.8 | 182318.7 | 134869.996 | 58101.243 |
| Cl_F_pred | mL/hr/kg | 15911.74 | 13016.27 | 18312.25 | 13714.9 | 11875.72 | 25713.82 | 16424.116 | 5094.453 |
| AUMC | hr * hr * ug/mL | 11.7827 | 17.1373 | 15.5268 | 17.06 | 25.4013 | 5.8624 | 15.462 | 6.478 |
| MRT | hr | 6.2495 | 7.4355 | 9.4777 | 7.7992 | 10.0553 | 5.0248 | 7.674 | 1.900 |

Group 1: Tramadol Pharmacokinetics

| | | | | | | | | Mean | Std. Dev. |
|---|---|---|---|---|---|---|---|---|---|
| Rsq | | 0.9907 | 0.9495 | 0.9991 | 0.9891 | 1 | 0.9842 | 0.985 | 0.019 |
| Lambda_z | 1/hr | 0.8741 | 0.7017 | 0.6628 | 0.5343 | 1.3173 | 0.4448 | 0.756 | 0.312 |
| Half-life | hr | 0.793 | 0.9878 | 1.0458 | 1.2974 | 0.5262 | 1.5584 | 1.035 | 0.364 |
| Tmax | hr | 2 | 2 | 1.5 | 4 | 8 | 1.5 | 3.167 | 2.543 |
| Cmax | ug/mL | 1.8593 | 0.8259 | 1.2633 | 2.7365 | 1.3706 | 1.56 | 1.603 | 0.652 |
| Tlast | hr | 22 | 20 | 20 | 24 | 24 | 16 | 21.000 | 3.033 |
| Clast | ug/mL | 0.0019 | 0.0044 | 0.0069 | 0.0131 | 0.0018 | 0.0107 | 0.006 | 0.005 |
| AUC(0_to_Clast) | hr * ug/mL | 13.1733 | 4.9998 | 9.2125 | 18.5038 | 15.7447 | 3.7965 | 10.905 | 5.909 |
| AUC(0_to_infinity) | hr * ug/mL | 13.1757 | 5.0074 | 9.2232 | 18.505 | 15.746 | 3.8009 | 10.910 | 5.906 |
| AUC_(%_extrap.) | % | 0.0182 | 0.1523 | 0.1161 | 0.0066 | 0.0086 | 0.1159 | 0.070 | 0.066 |
| Vz_F_pred | mL/kg | 2604.899 | 8537.772 | 4907.703 | 3034.495 | 1446.345 | 17745.94 | 6379.526 | 6095.786 |
| Cl_F_pred | mL/hr/kg | 2276.914 | 5991.128 | 3252.674 | 1621.186 | 1905.244 | 7892.812 | 3823.326 | 2549.728 |
| AUMC | hr * hr * ug/mL | 85.1731 | 30.6714 | 57.3122 | 116.3354 | 123.615 | 11.0943 | 70.700 | 45.665 |
| MRT | hr | 6.4644 | 6.1252 | 6.2139 | 6.2867 | 7.8506 | 2.9188 | 5.977 | 1.629 |

| | | Dog_Number | | | | | | | |
|---|---|---|---|---|---|---|---|---|---|
| Paramaeter | Units | 204 | 205 | 208 | 211 | 221 | 223 | Mean | Std. Dev. |

Group 2: M1 Pharmacokinetics

| | | | | | | | | | |
|---|---|---|---|---|---|---|---|---|---|
| Rsq | | 1 | 0.9808 | 0.9851 | 0.8214 | 0.8433 | 0.9373 | 0.928 | 0.077 |
| Lambda_z | 1/hr | 0.1353 | 0.3977 | 0.206 | 0.0588 | 0.1216 | 0.218 | 0.190 | 0.118 |
| Half-life | hr | 5.1215 | 1.7428 | 3.3651 | 11.7918 | 5.6979 | 3.1789 | 5.150 | 3.552 |
| Tmax | hr | 1 | 3 | 1 | 3 | 1 | 3 | 2.000 | 1.095 |
| Cmax | ug/mL | 0.1632 | 0.1565 | 0.2174 | 0.2943 | 0.1477 | 0.1608 | 0.190 | 0.057 |
| Tlast | hr | 36 | 22 | 18 | 36 | 22 | 18 | 25.333 | 8.454 |
| Clast | ug/mL | 0.0074 | 0.0017 | 0.0328 | 0.0148 | 0.026 | 0.0093 | 0.015 | 0.012 |
| AUC(0_to_Clast) | hr * ug/mL | 1.591 | 1.2023 | 1.7833 | 2.3962 | 1.4456 | 1.3324 | 1.625 | 0.428 |
| AUC(0_to_infinity) | hr * ug/mL | 1.6456 | 1.2074 | 1.9379 | 2.6115 | 1.6477 | 1.3889 | 1.740 | 0.495 |
| AUC_(%_extrap.) | % | 3.3185 | 0.425 | 7.978 | 8.2452 | 12.266 | 4.0697 | 6.050 | 4.247 |
| Vz_F_pred | mL/kg | 134699.6 | 62473.13 | 75157.07 | 195427.9 | 149670.3 | 99056.85 | 119414.158 | 50085.061 |
| Cl_F_pred | mL/hr/kg | 18230.26 | 24846.88 | 15480.72 | 11487.72 | 18207.25 | 21599.28 | 18308.684 | 4650.063 |
| AUMC | hr * hr * ug/mL | 22.1431 | 8.5922 | 16.2483 | 34.518 | 20.0062 | 10.1029 | 18.602 | 9.442 |
| MRT | hr | 13.4558 | 7.1163 | 8.3845 | 13.2178 | 12.1419 | 7.2738 | 10.265 | 2.994 |

Group 2: Tramadol Pharmacokinetics

| | | | | | | | | | |
|---|---|---|---|---|---|---|---|---|---|
| Rsq | | 0.8808 | 0.9736 | 0.9874 | 0.9501 | 0.8909 | 0.9989 | 0.947 | 0.050 |
| Lambda_z | 1/hr | 0.0945 | 0.494 | 0.4987 | 0.3692 | 0.3841 | 0.4376 | 0.380 | 0.150 |
| Half-life | hr | 7.3337 | 1.4031 | 1.39 | 1.8775 | 1.8046 | 1.5838 | 2.565 | 2.345 |
| Tmax | hr | 6 | 6 | 6 | 3 | 10 | 8 | 6.500 | 2.345 |
| Cmax | ug/mL | 0.5968 | 2.1666 | 2.936 | 2.9567 | 0.5351 | 1.8789 | 1.845 | 1.077 |
| Tlast | hr | 24 | 18 | 18 | 36 | 22 | 16 | 22.333 | 7.312 |
| Clast | ug/mL | 0.0926 | 0.0291 | 0.0819 | 0.0113 | 0.0593 | 0.0828 | 0.060 | 0.033 |
| AUC(0_to_Clast) | hr * ug/mL | 7.6339 | 12.7417 | 22.9313 | 17.2425 | 4.456 | 13.2268 | 13.039 | 6.611 |
| AUC(0_to_infinity) | hr * ug/mL | 8.5754 | 12.7988 | 23.1066 | 17.243 | 4.5881 | 13.4111 | 13.287 | 6.484 |
| AUC_(%_extrap.) | % | 10.9798 | 0.446 | 0.7586 | 0.0027 | 2.8794 | 1.3744 | 2.740 | 4.158 |
| Vz_F_pred | mL/kg | 37013.8 | 4744.666 | 2603.641 | 4712.522 | 17022.98 | 5111.353 | 11868.160 | 13358.955 |
| Cl_F_pred | mL/hr/kg | 3498.366 | 2343.972 | 1298.329 | 1739.838 | 6538.703 | 2236.951 | 2942.693 | 1910.361 |
| AUMC | hr * hr * ug/mL | 114.4944 | 92.5742 | 180.2629 | 125.5943 | 58.4876 | 103.4698 | 112.481 | 40.406 |
| MRT | Hr | 13.3514 | 7.233 | 7.8014 | 7.2838 | 12.7478 | 7.7152 | 9.355 | 2.877 |

As shown in FIGS. 3A and 3B, both the uncoated (Group No. 1, FIG. 3A) and coated (Group No. 2, FIG. 3B) tablets exhibited sustained blood concentration profiles for tramadol and M1.

Example 4

In Vivo Gastric Retention Study of Tramadol SR Matrix Tablets

In another in vivo study, the coated tramadol SR tablets prepared according to Example 1 were administered orally to beagle dogs of an approximate body weight of 10 kg. Three (3) hours after the dosing, the dogs were humanely sacrificed and gastric and intestinal contents were recovered. A non-disintegrated, deformed and swollen tablet mass was found in the small intestine region. This indicates that the tablets stayed in the dog stomach for maximal three hours whereas the observed sustained release of tramadol lasted for 12-16 hours, suggesting that the prolonged blood concentration profile of tramadol was not caused by gastric retention of the tablet. It is concluded that matrix SR tablets disclosed in this invention are not gastric retention tablets.

Example 5

Stability Analysis of Tramadol SR Matrix Tablets

Coated tramadol HCl SR tablets prepared according to Example 1 were packaged in plastic screw cap bottle (high density polyethylene) without desiccant and stored at 25° C./60% relative humidity. Tablet samples were removed at designated time points and analyzed by HPLC for tramadol stability. The amounts of tramadol HCl in a tablet (strength) are listed below:

|  | Initial | 7 months | 18 months |
|---|---|---|---|
| Avg. strength (mg tramadol HCL/tablet, n = 6) | 614.9 | 628.7 | 637.3 |
| % label claim | 102.5 | 104.8 | 104.5 |

The above stability data suggests that the tramadol HCl SR tablets prepared according to the composition and method disclosed in the invention are stable and suitable for commercialization.

Example 6

Composition, Method of Preparation, and In Vitro Dissolution Study of Glucosamine SR Matrix Tablets Glucosamine is an amino sugar and has been used extensively for joint health. It has been shown in clinical trials for decades to be effective at easing the joint discomfort and largely increasing flexibility. Some studies even indicate that glucosamine may help rebuild cartilage—something traditional NSAID pain relievers are unable to do.

Glucosamine is normally available as a hydrochloride salt, which is extremely soluble in water (dissolves in water in any proportion). Glucosamine is also a high dose drug with unit dose up to 1000-1500 mg. Due to its fast metabolism (short half life), glucosamine in a conventional tablet form (i.e., non-sustained release or immediate-release tablet) is required for 3-6 times daily dosing. Thus, glucosamine HCl is a perfect example of a drug with a high solubility, high dose and short half-life, which makes it a good candidate for the matrix SR tablet composition and method of preparation disclosed in this invention. Almost all currently available commercial products of glucosamine are of the immediate-release formulation.

Other than inconvenience of the 3-6 times daily dosing, the immediate-release glucosamine formulations deliver a burst of glucosamine that spikes almost immediately after administration. A complicating factor to consider is an associated insulin spike (glucosamine is structurally similar to glucose, which triggers insulin release), and possibly wasted glucosamine with a very high dose released in a short time, since the oral bioavailability (amount of drug absorbed) of many highly water soluble drugs does not correlate linearly with the dose given (such as gabapentin), i.e., the larger the dose of a highly water soluble drug is given, the greater percent of the drug is not absorbed and thus more drug gets wasted.

Therefore, a glucosamine SR tablet is expected to have the following advantages:

(1) Convenience in dosing, i.e., twice-a-day or once-a-day.

(2) Less complication associated with insulin spike, which is particularly important in diabetes patients.

(3) Reduce the total daily dose by improving bioavailability.

Glucosamine SR matrix tablets were prepared using the compositions and methods disclosed in this application. SR matrix tablets containing only glucosamine HCl and glucosamine HCl in combination with chondroitin sulfate, which is another common agent used for joint health, were prepared with the following composition using a method similar to that described in Example 1.

|  | Component | % w/w | Mg per tablet |
|---|---|---|---|
| Glucosamine ONLY | Glucosamine HCl, micronized | 60 | 600 |
|  | HPMC (Methocel K100M Premium CR) | 22.4 | 224 |
|  | Microcrystalline cellulose (AVICEL PH 102) | 15.6 | 156 |
|  | Magnesium stearate, USP | 2 | 20 |
|  | Total |  | 1000 |
| Glucosamine-chondroitin Combination | Glucosamine HCl, micronized | 40 | 400 |
|  | Chondroitin sulfate, micronized | 30 | 300 |
|  | Manganese | 0.5 | 5 |
|  | Vitamin C | 2 | 20 |
|  | HPMC (Methocel K100M Premium CR) | 23 | 230 |
|  | Microcrystalline cellulose (AVICEL PH 102) | 2.5 | 25 |
|  | Magnesium stearate, USP | 2 | 20 |
|  | Total | 100 | 1000 |

Figure 4:
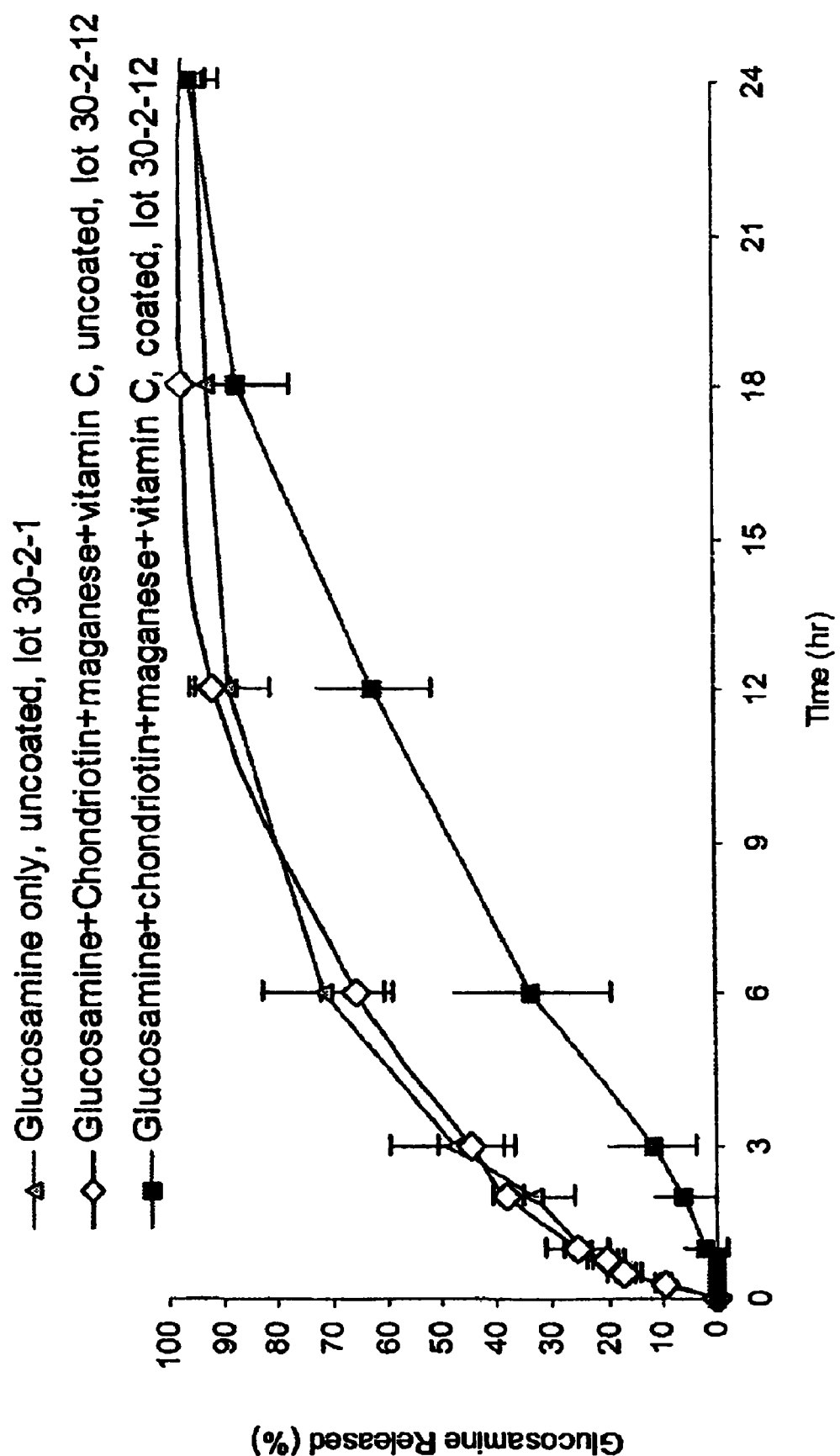
FIG. 4 is a graph that shows the in vitro release of glucosamine hydrochloride from a matrix tablet prepared according to Example 6.

The in vitro release profiles of glucosamine from the SR matrix tablets are shown in FIG. 4. The uncoated tablets provided a sustained release of glucosamine for about 12 hours and the coated for about 18 hours. The SR matrix tablet composition and method of making disclosed in the application can be applied to glucosamine HCl and chondroitin sulfate—two drugs of a highly water solubility, high dose and short half-life.

Example 7

Composition and Method of Acetaminophen SR Matrix Tablets

Acetaminophen is another drug of high water solubility, high dose and short half-life. It is commonly available under a trade name of TYLENOL®. For pain control or fever reduction, TYLENOL® is taken orally every 4 hours (6 times a day). Acetaminophen SR matrix tablets can be prepared using the compositions and methods of disclosed in this application. For example, acetaminophen SR matrix tablets with the following composition may be prepared using a method similar to that described in Example 1.

| Component | % w/w | Mg per tablet | Mg per tablet |
|---|---|---|---|
| Acetaminophen, micronized | 60 | 600 | 900 |
| HPMC (Methocel K100M Premium CR) | 22.4 | 224 | 335 |
| Microcrystalline cellulose (AVICEL PH 102) | 15.6 | 156 | 234 |
| Magnesium stearate, USP | 2 | 20 | 30 |
| Total | 100 | 1000 | 1500 |

Example 8

Composition and Method of Preparing Gabapentin SR Matrix Tablets

Gabapentin is indicated for seizure control and has been used for neuropathic pain. It is freely soluble in water. The current immediate release tablets (NEURONTIN®) are given orally to an adult patient at 900-1800 mg/day in three divided doses, i.e., three times a day and 300-600 mg each time. Because of the high dose requirement, the NEURONTIN® 800 mg tablet is regarded as one of the largest prescription tablets available. With an elimination half-life of about 5-7 hours, gabapentin makes another good candidate drug for SR delivery using the matrix SR tablet composition and method of making disclosed in this application.

Gabapentin SR matrix tablets can be prepared using the compositions and methods disclosed in this application. For example, gabapentin SR matrix tablets with the following composition may be prepared using a method similar to that described in Example 1.

| Component | % w/w | Mg per tablet |
|---|---|---|
| Gabapentin, micronized | 60 | 900 |
| HPMC (Methocel K100M Premium CR) | 22.4 | 335 |
| Microcrystalline cellulose (AVICEL PH 102) | 15.6 | 234 |
| Magnesium stearate, USP | 2 | 30 |
| Total | 100 | 1500 |

The gabapentin SR tablets in this example may be taken once-a-day while providing the efficacious blood concentration level for its indications.

Example 9

Comparative In Vitro Dissolution Studies Between ULTRAM® Tablets and Tramadol SR Matrix Tablets Coated ER tablets containing 300 mg tramadol HCl were prepared using a method similar to that described in Example 1. The components and their concentrations of these tablets are shown in the tables below:

Uncoated Matrix Tablet

| Component | % w/w | Mg per tablet |
|---|---|---|
| Tramadol HCl, micronized* | 43.0 | 300 |
| Hydroxypropyl Methylcellulose, USP | 33.0 | 230 |
| Microcrystalline Cellulose, NF | 23.0 | 160 |
| Magnesium Stearate, NF | 1.0 | 7 |
| Total | 100 | 697 |

Coating Dispersion

| Function | Component | Mg/tablet |
|---|---|---|
| Barrier Coating | Surelease E-7-19010 suspension (Solids content 25.0% w/w) | 47.4 |
| Solution | Opadry II Clear Y-19-7483 | 2.1 |
|  | Purified Water USP to dilute | — |
| Yellow Film Coating | Opadry II Yellow 85F92077 | 13.9 |
|  | Purified Water USP to dilute | — |
|  | Carnauba Wax NF | 0.10 |

Figure 5:
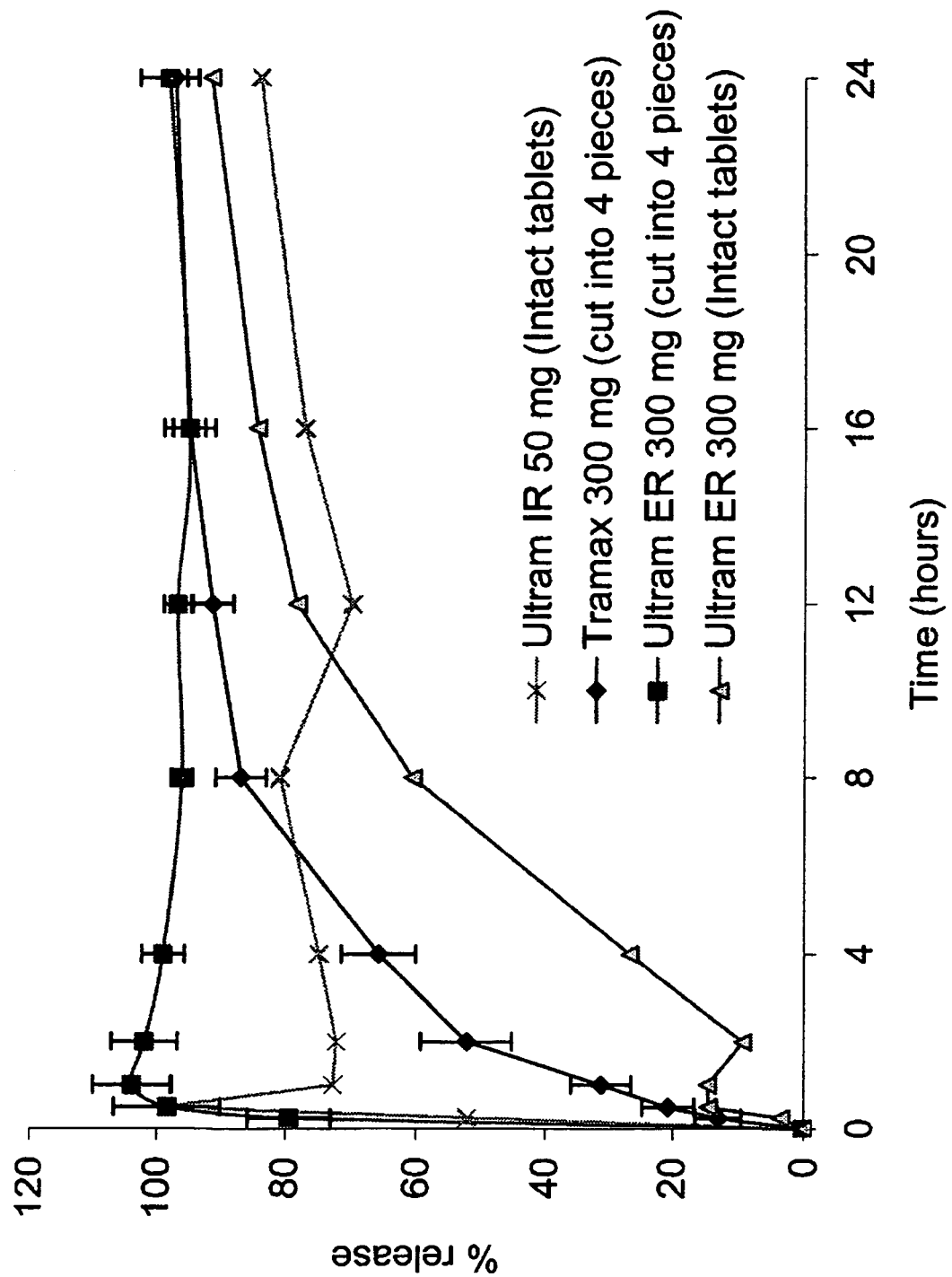
FIG. 5 is a graph that shows in vitro release of tramadol from ULTRAM® ER 300 mg and a tramadol HCl ER matrix tablet prepared according to Example 3 of the present invention. Both tablets were cut into four sections about equal size to simulate tablet fractions after being chewed by animal patients.

In vitro dissolution of the SR tablets containing 300 mg tramadol HCl (intact tablets and tablets cut into four pieces) was compared to that of ULTRAM® ER 300 mg tablets (intact tablets and tablets cut into four pieces, respectively) using the method described in U.S. Pat. No. 6,254,887 (i.e., the Ph. Eur. Paddle Method at 100 rpm in 900 ml 0.1 N hydrochloric acid at 37° C. and using UV detection at 270 nm). The results are shown in FIG. 5 and the table below.

| Tablet | Time (hr) | Avg dissolution (%, n = 4 tablets)* | Std Dev |
|---|---|---|---|
| Ultram ® ER 300 mg tablet cut into 4 fragments about the same size | 0 | 0.0 | 0.0 |
| | 0.25 | 79.4 | 6.2 |
| | 0.5 | 98.3 | 8.3 |
| | 1 | 103.8 | 6.0 |
| | 2 | 101.9 | 5.0 |
| | 4 | 99.1 | 3.3 |
| | 8 | 96.3 | 1.6 |
| | 12 | 97.1 | 2.1 |
| | 16 | 95.3 | 4.0 |
| | 24 | 98.7 | 4.5 |
| Tramadol ER 300 mg tablet prepared according to Example 1 cut into 4 fragments about the same size | 0 | 0 | 0.0 |
| | 0.25 | 13.0 | 3.5 |
| | 0.5 | 20.7 | 4.0 |
| | 1 | 31.1 | 4.6 |
| | 2 | 52.3 | 7.0 |
| | 4 | 65.8 | 5.6 |
| | 8 | 87.0 | 3.9 |
| | 12 | 91.5 | 3.2 |
| | 16 | 95.47 | 2.55 |
| | 24 | 97.86 | 1.76 |

*Using the method as described in the Claim 1 of U.S. Pat. No. 6,254,887

ULTRAM® ER tablets exhibited sustained release property only when the tablets were intact. When ULTRAM® ER tablets were cut into four pieces, they lost the sustained release property and essentially became an immediate release formulation that released an entire day's dose in one quick release (burst). Such a burst would cause significant safety concerns to non-human patients such as cats, dogs, or horses who likely chew the tablets. Therefore, ULTRAM® ER tablets or other sustained release technology that depend on a coating as the drug release barrier are deemed unsuitable for animal use. In comparison, the matrix tablets prepared according to this invention maintained the in vitro sustained release property even when the tablets have been cut into four pieces.

Example 10

In Vivo Pharmacokinetic Studies of Intact v. Crushed Tramadol SR Matrix Tablets

Coated sustained release tablets containing 300 mg tramadol HCl were prepared using a method similar to that described in Example 1. The components and their concentrations of these tablets are shown in the tables in Example 9. They were administered orally to dogs at 15±2 mg/kg as halves of 300 mg tablets or as crushed halves of 300 mg tablets. The doges were fed twice daily and not fasted prior to administration of the tablets. Blood samples were taken at various time points and analyzed by high performance liquid chromatography for plasma tramadol concentrations.

Figure 6:
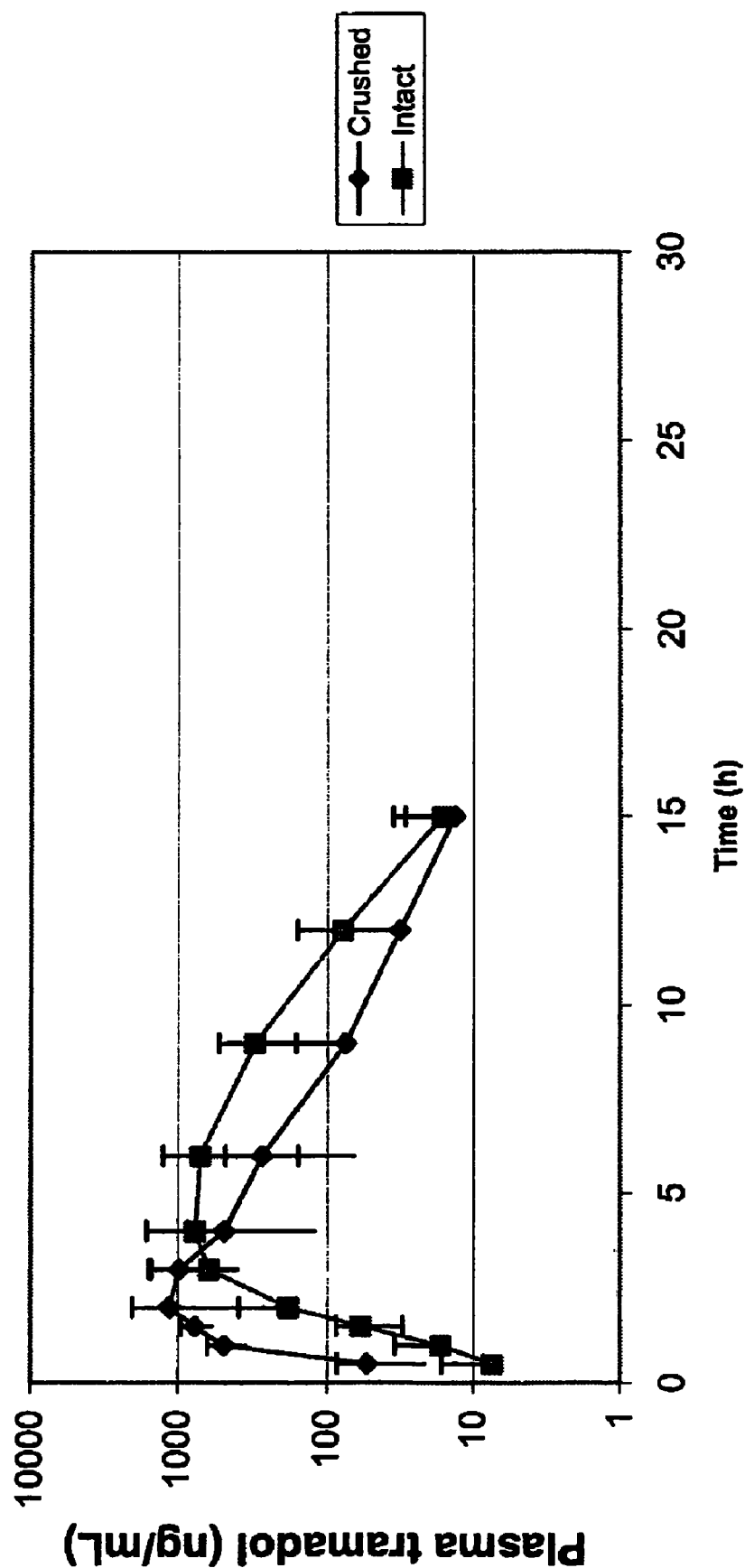
FIG. 6 is a graph that shows blood concentrations of tramadol HCl in Beagle dogs administered with either crushed or intact SR matrix tablets containing 300 mg tramadol HCl at a dose of approximate 15 mg/kg.
Figure 7:
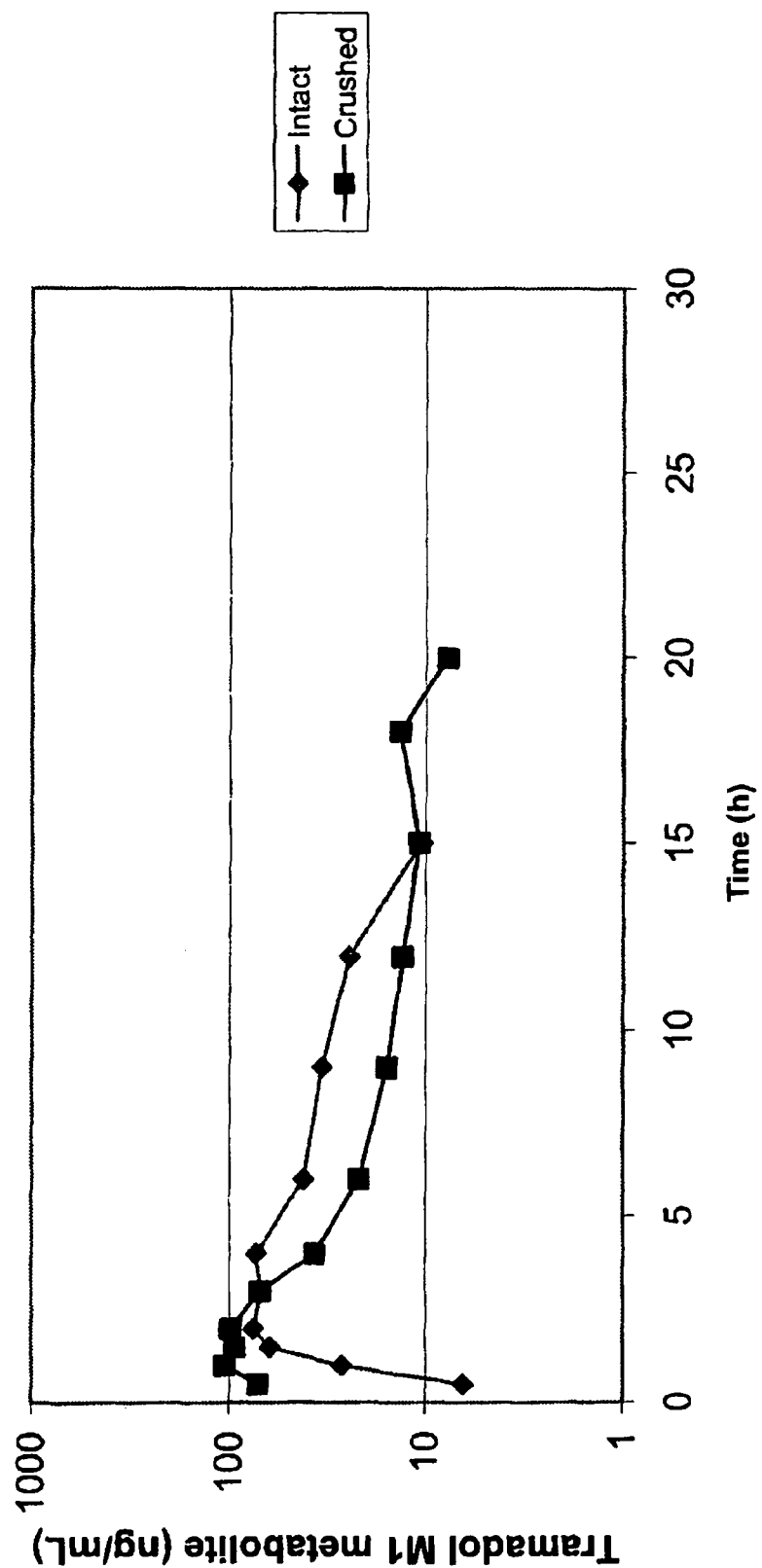
FIG. 7 is a graph that shows blood concentrations of tramadol HCl M1 metabolite in Beagle dogs administered with either crushed or intact SR matrix tablets containing 300 mg tramadol HCl at a dose of approximate 15 mg/kg.

The results shown that both crushed and intact tablets exhibited sustained blood tramadol concentration profiles (FIG. 6) and sustained blood concentration profiles of the active metabolite of tramadol, M1 (FIG. 7). It is thus concluded that such tablets are of particular use for veterinarian applications where intact tablets are likely to be chewed upon by animal patients.

Example 11

In Vitro Dissolution Studies of Tramadol SR Matrix Tablets of Various Dosages

Coated tablets containing 90 mg, 180 mg, 300 mg, or 600 mg tramadol HCl were prepared using a method described in Example 1 or a method similar to that described in Example 1. The components and their concentrations of the tablets containing 300 mg tramadol HCl are shown in the tables in Example 9. The components and their concentrations of the tablets containing 90 mg, 180 mg, and 600 mg tramadol HCl are shown in the tables below.

Tablets Containing 90 mg Tramadol HCl
  Uncoated Matrix Tablet

| Component | % w/w | Mg per tablet |
|---|---|---|
| Tramadol HCl, micronized* | 20 | 1083 |
| Hydroxypropyl Methylcellulose, USP | 46.4 | 209.7 |
| Microcrystalline Cellulose, NF | 32.4 | 145.8 |
| Magnesium Stearate, NF | 1 | 4.5 |
| Total | 100 | 450 |

Coating Dispersion

| Function | Component | Mg/tablet |
|---|---|---|
| Barrier Coating Solution | Surelease E-7-19010 suspension (Solids content 25.0% w/w) | 30.6 |
| | Opadry II Clear Y-19-7483 | 1.35 |
| | Purified Water USP to dilute | — |
| Yellow Film Coating | Opadry II Yellow 85F92077 | 9.0 |
| | Purified Water USP to dilute | — |
| | Carnauba Wax NF | 0.2 |

Tablets Containing 180 mg Tramadol HCl
  Uncoated Matrix Tablet

| Component | % w/w | Mg per tablet |
|---|---|---|
| Tramadol HCl, micronized* | 31.3 | 180 |
| Hydroxypropyl Methylcellulose, USP | 40 | 230 |
| Microcrystalline Cellulose, NF | 27.8 | 160 |
| Magnesium Stearate, NF | 1 | 5.8 |
| Total | 100 | 575.8 |

Coating Dispersion

| Function | Component | Mg/tablet |
|---|---|---|
| Barrier Coating Solution | Surelease E-7-19010 suspension (Solids content 25.0% w/w) | 43.1 |
| | Opadry II Clear Y-19-7483 | 1.9 |
| | Purified Water USP to dilute | — |
| Yellow Film Coating | Opadry II Yellow 85F92077 | 13.8 |
| | Purified Water USP to dilute | — |
| | Carnauba Wax NF | 0.2 |

Tablets Containing 600 mg Tramadol HCl
  Uncoated Matrix Tablet

| Component | % w/w | Mg per tablet |
|---|---|---|
| Tramadol HCl, micronized* | 43 | 300 |
| Hydroxypropyl Methylcellulose, USP | 33 | 230 |
| Microcrystalline Cellulose, NF | 23 | 160 |
| Magnesium Stearate, NF | 1 | 7 |
| Total | 100 | 697 |

Coating Dispersion

| Function | Component | Mg/tablet |
|---|---|---|
| Barrier Coating Solution | Surelease E-7-19010 suspension (Solids content 25.0% w/w) | 47.4 |
| | Opadry II Clear Y-19-7483 | 2.1 |
| | Purified Water USP to dilute | — |
| Yellow Film Coating | Opadry II Yellow 85F92077 | 13.9 |
| | Purified Water USP to dilute | — |
| | Carnauba Wax NF | 0.1 |

Figure 8:
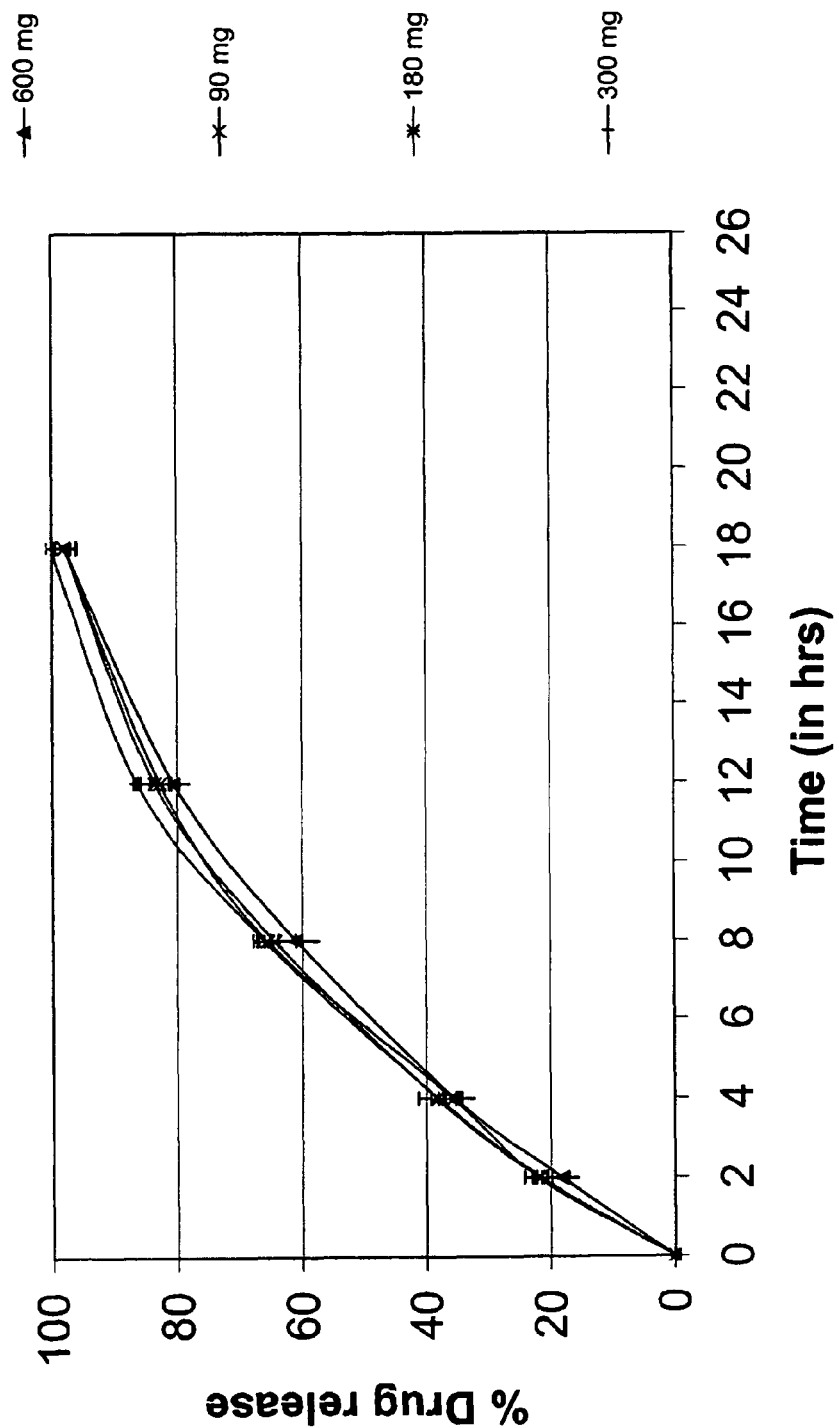
FIG. 8 is a graph that shows in vitro dissolution of SR matrix tablets containing 90 mg, 180 mg, 300 mg, or 600 mg tramadol HCl.

The in vitro dissolution study was performed using the rotating basket method USP Apparatus 1 (USP <711>). The results from these tablets show that all the coated tablets exhibited sustained release characteristics for about 18 hours (FIG. 8).

Example 12

Figure 9:
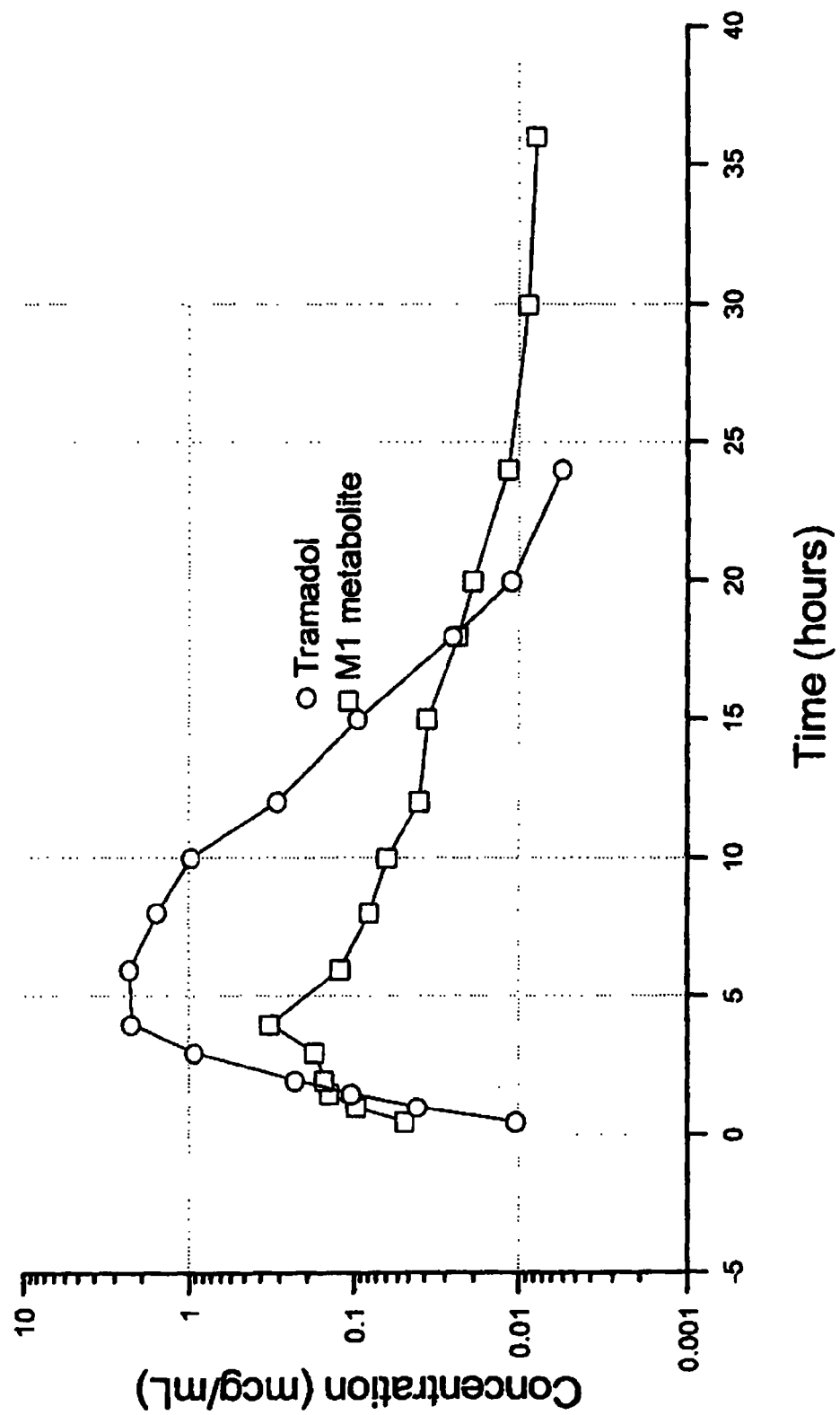
FIG. 9 is a graph that shows plasma concentrations of tramadol and its active metabolite M1 in dogs administered at 30 mg/kg as single ER matrix tablets containing 300 mg tramadol HCl. The dogs were fed immediately before dosing.
Figure 10:
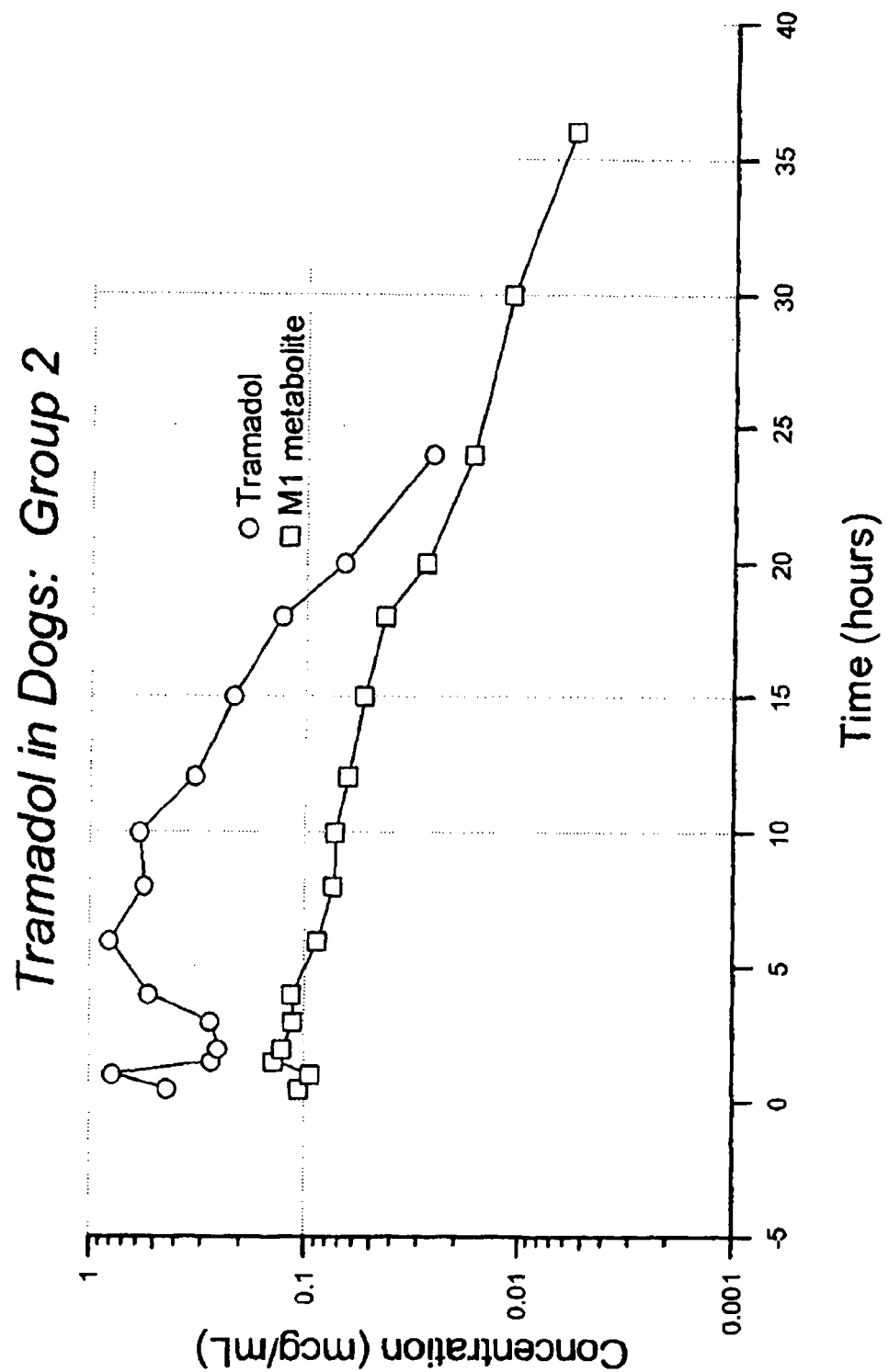
FIG. 10 is a graph that shows plasma concentrations of tramadol and its metabolite M1 in dogs administered at 30 mg/kg as single ER matrix tablets containing 300 mg tramadol HCl. The dogs were fasted for 12 hours, dosed, and fasted for another 4 hours.
Figure 11:
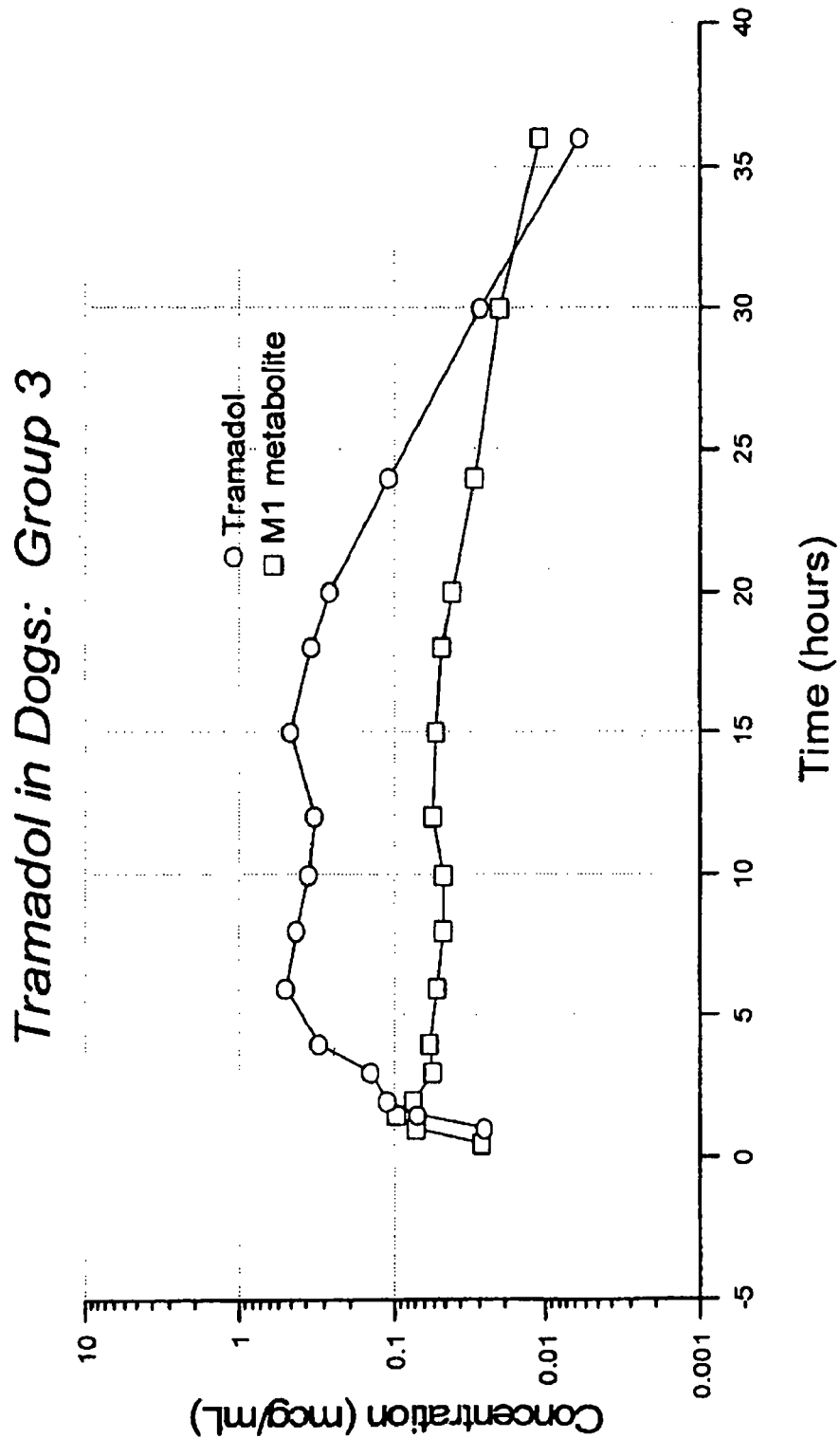
FIG. 11 is a graph that shows plasma concentrations of tramadol and its metabolite M1 in dogs administered at 30 mg/kg as single ER matrix tablets containing 300 mg tramadol HCl. The dogs were fasted for 12 hours, dosed, and fasted for another 12 hours.

In Vivo Pharmacokinetic Studies of Tramadol SR Matrix Tables Administered to Dogs Under Various Feeding and Dosing Conditions In one study, SR tablets containing 300 mg tramadol HCl were prepared using a method similar to that described in Example 1. The components and their concentrations of the tablets are shown in the tables in Example 9. The tablets were administered at 30 mg/kg as single 300 mg tablets to dogs under various feeding and dose conditions. Blood samples were taken at various time points and analyzed by high performance liquid chromatography for plasma tramadol and its metabolite (M1) concentrations. Group No. 1 were dogs fed immediately before dosing, Group No. 2 dogs fasted 12 hours, dosed, and fasted another 4 hours, and Group No. 3 dogs fasted 12 hours, dosed, and fasted another 12 hours. The pharmacokinetic profiles of tramadol and M1 in various groups of dogs are shown in FIG. 9 (Group No. 1), FIG. 10 (Group No. 2), and FIG. 11 (Group No. 3).

Figure 12:
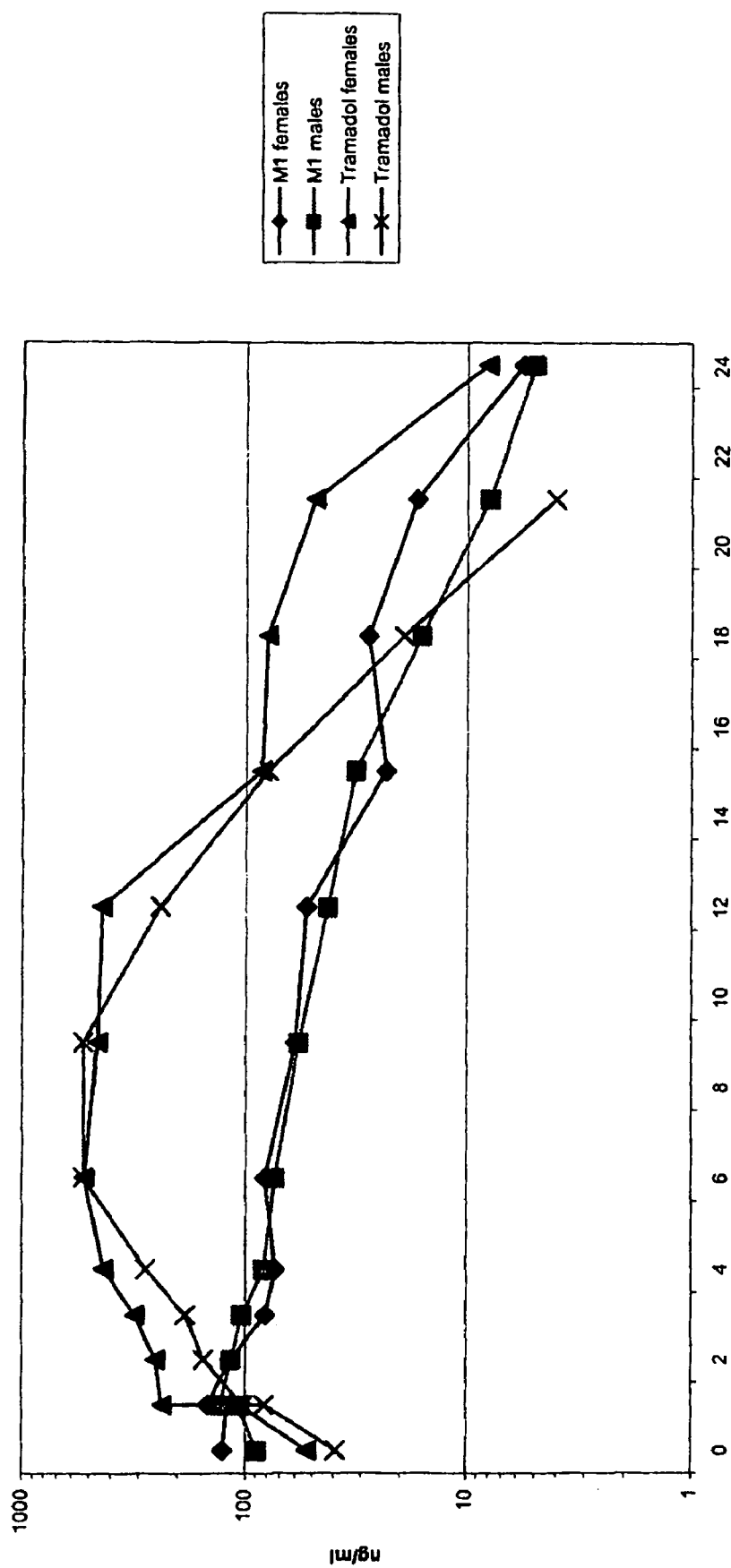
FIG. 12 is a graph that shows plasma concentrations of tramadol and its metabolite M1 in male and female dogs administered at approximately 18 mg/kg as single ER matrix tablets containing 180 mg tramadol HCl. The dogs were fasted for 12 hours and fed within 30 minutes for dosing.

In another study, ER tablets containing 180 mg tramadol HCl were prepared using a method similar to that described in Example 1. The components and their concentrations of the tablets are as shown in Example 11. The tablets were administered at 18 mg/kg as single 180 mg tablets to male and female dogs that were fasted 12 hours and fed within 30 minutes for dosing. Blood samples were taken at various time points and analyzed by high performance liquid chromatography for plasma tramadol and its metabolite (M1) concentrations. The pharmacokinetic profiles of tramadol and M1 are shown in FIG. 12.

The results of both studies shown that both tramadol and its active metabolite, M1, were present for an extended period of time in dog blood under various feeding and dosing conditions.

Example 13

Figure 13:
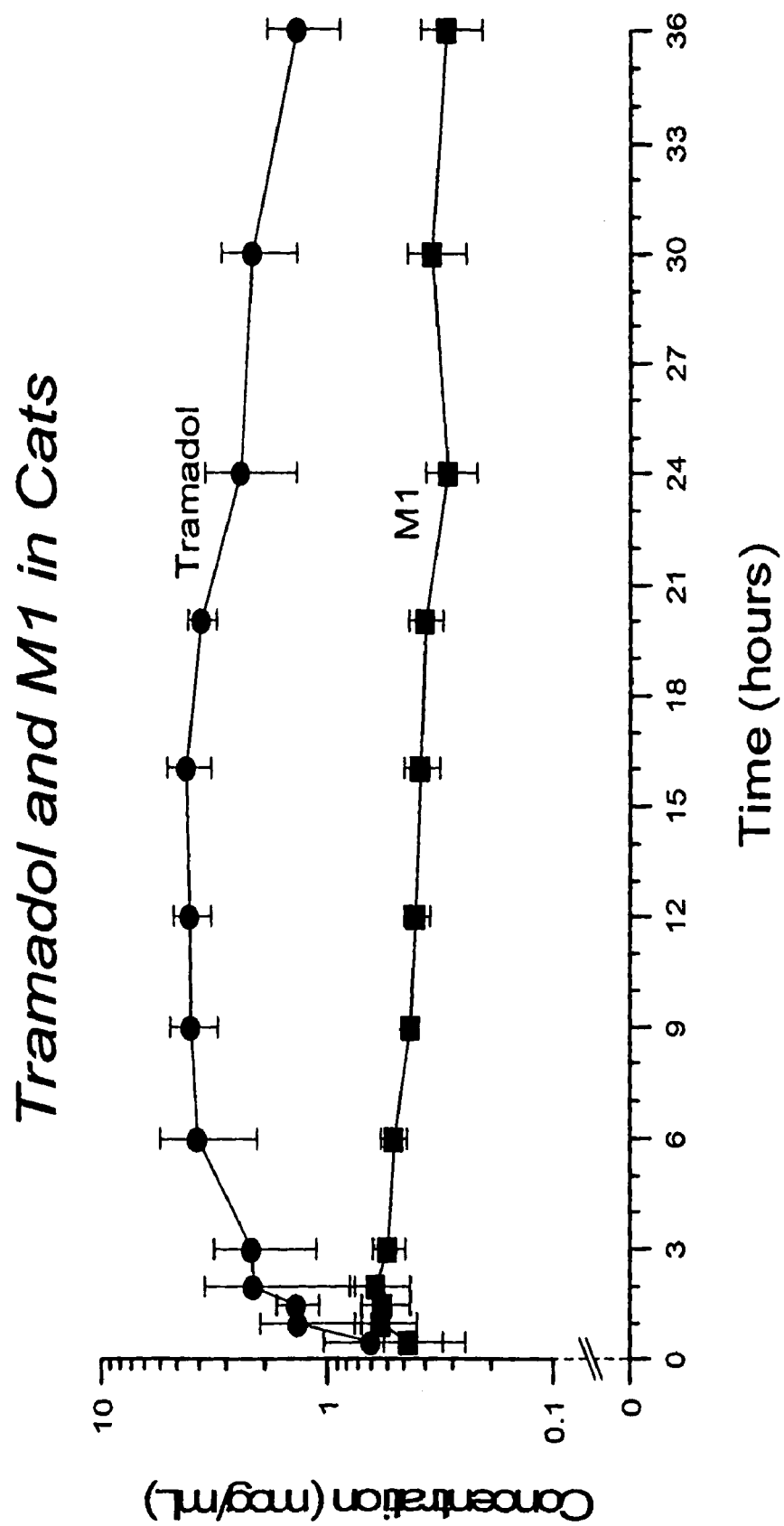
FIG. 13 is a graph that shows plasma concentrations of tramadol and its metabolite M1 in cats treated at 30 mg/kg via administration of halves of ER matrix tablets containing 300 mg tramadol HCl.

In Vivo Pharmacokinetic Study of Tramadol Matrix Tablets Administered in Cats Coated ER tablets containing 300 mg tramadol HCl were prepared using a method similar to that described in Example 1. The components and their concentrations are shown in the tables in Example 9. The tablets were administered at 30 mg/kg as halves of single 300 mg tablets to cats that were fasted prior to administration and offered food no less than 1 hour after dosing. Blood samples were taken at various time points and analyzed by high performance liquid chromatography for plasma tramadol and its metabolite (M1) concentrations. The resulting pharmacokinetic profiles (FIG. 13) show that both tramadol and M1 were present for an extended period of time in cat blood.

Example 14

In Vivo Pharmacokinetic Study of Glucosamine SR Matrix Tablets

Four uncoated matrix tablets prepared in a manner similar to that cited in Example 1 were administered to fasted beagle dogs at a glucosamine dose of 1600 mg/dog. Each tablet contains 400 mg glucosamin hydrochloride, 200 mg chondroitin sulfate, 20 mg Ester-C™ (vitamin C), 5 mg manganese sulfate, 230 mg HPMC, 135 mg microcrystalline cellulose, and 10 mg magnesium stearate. Blood samples were taken and analyzed by high performance liquid chromatography coupled with a mass spectrometer (LC-MS) for concentration of glucosamine.

Figure 14:
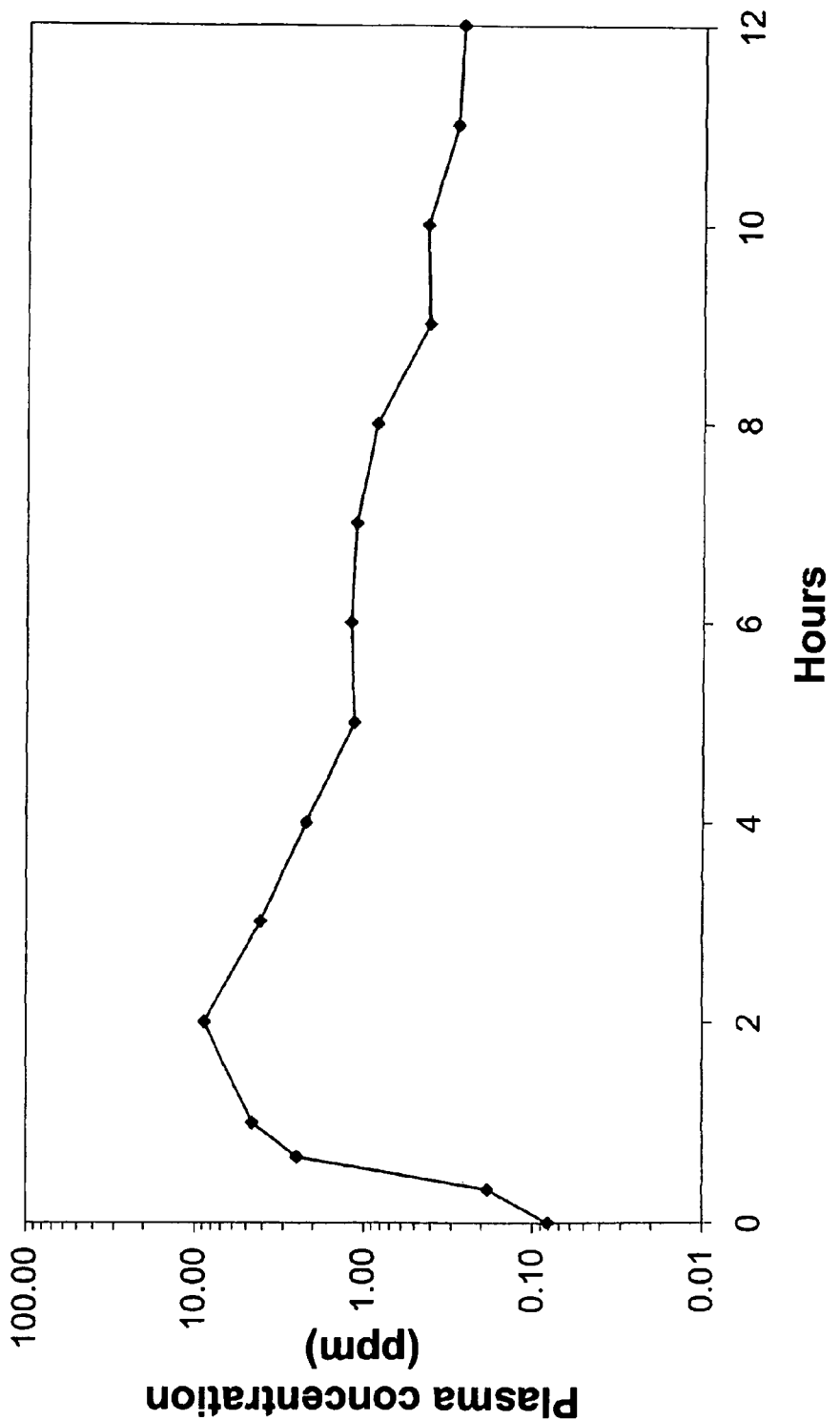
FIG. 14 is a graph that shows plasma concentrations of glucosamine in fasted Beagle dogs received 1600 mg of an SR formulation of glucosamine as an uncoated matrix tablet.

The resulting pharmacokinetic profile of glucosamine shows that glucosamine was present for an extended period of time in plasma (FIG. 14).

All of the above U.S. patents, U.S. patent application publications, U.S. patent applications, foreign patents, foreign patent applications and non-patent publications referred to in this specification, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A sustained release matrix pharmaceutical composition, wherein the composition is in the form of an orally deliverable tablet, said composition prepared by the steps comprising:
   (i) micronizing a pharmaceutically active agent, wherein said pharmaceutically active ingredient is tramadol hydrochloride, which is freely soluble in water, wherein the pharmaceutically active agent is micronized to a particle size having an upper size limit of about or less than 125 micron (120 mesh) and a lower size limit of about or greater than 74 micron (200 mesh);
   (ii) combining said pharmaceutically active ingredient and a hydrophilic polymer, wherein said hydrophilic polymer is hydroxypropyl methylcellulose at 22.4% w/w;
   (iii) dry blending the micronized pharmaceutically active agent and said hydrophilic polymer to form a powder blend; and
   admixing the powder blend with microcrystalline cellulose present at 15.6% w/w and magnesium stearate present at 2.0% w/w;
   (iv) compressing the powder blend into said sustained release matrix pharmaceutical composition in the form of a tablet comprising a layer of film using a coating composition comprising an aqueous dispersion containing ethyl cellulose, oleic acid, ammonium hydroxide and water and a solution containing polyethylene glycol.

2. The composition of claim 1 wherein the pharmaceutically active agent contributes about or greater than 15% of the total weight of the pharmaceutical composition.

3. The composition of claim 1 wherein the pharmaceutically active agent contributes about or greater than 50% of the total weight of the pharmaceutical composition.

4. The composition of claim 1 wherein the composition is in the form of a crushed orally deliverable tablet.

5. The composition of claim 1 wherein the composition is in the form of a fragmented orally deliverable tablet.

6. The composition of claim 1 wherein the pharmaceutically active agent is therapeutically effective at a daily dose of about or greater than 100 milligrams for an adult human patient.

7. The composition of claim 1 wherein the pharmaceutically active agent is present in an amount of about 50% to about 80% by weight.

8. The composition of claim 1 further comprising a second pharmaceutically active agent.

9. The composition of claim 8 wherein the pharmaceutically active agent is tramadol hydrochloride and the second pharmaceutically active agent is acetaminophen, carprofen, aspirin, glucosamine, meloxicam or celecoxib, or a pharmaceutically acceptable salt thereof.

10. The composition of claim 1 wherein said coating is a release-controlling layer.

11. The composition of claim 1 wherein said coating layer constitutes about 1% to about 5% by weight of the tablet.

12. The composition of claim 1 wherein the composition, upon oral administration to a patient in need thereof, provides extended release for at least about 12 hours.

13. The composition of claim 1 wherein the composition, upon oral administration to a patient in need thereof, provides a plasma concentration at or above a therapeutically effective concentration for a period of time that is at least 50% longer than an immediate release formulation containing the same amount of the pharmaceutically active agent.

14. The pharmaceutical composition of claim 1 wherein the composition is suitable for administration to a patient in need thereof no more than twice a day.

15. The composition of claim 2 wherein the tablet is processed by a direct compression method.

* * * * *